(12) United States Patent
Chen et al.

(10) Patent No.: US 11,737,659 B2
(45) Date of Patent: Aug. 29, 2023

(54) SURGICAL TISSUE PROTECTION SHEATH

(71) Applicant: SPIWay LLC, Carlsbad, CA (US)

(72) Inventors: Eugene Chen, Carlsbad, CA (US); Richard C. Ewers, Carlsbad, CA (US); Cang Lam, Irvine, CA (US); Stephanie Frimond, Carlsbad, CA (US)

(73) Assignee: SPIWay LLC, Carlsbad, CA (US)

( * ) Notice: Subject to any disclaimer, the term of this patent is extended or adjusted under 35 U.S.C. 154(b) by 153 days.

(21) Appl. No.: 17/152,559

(22) Filed: Jan. 19, 2021

(65) Prior Publication Data

US 2021/0137364 A1    May 13, 2021

Related U.S. Application Data

(63) Continuation of application No. 16/211,776, filed on Dec. 6, 2018, now Pat. No. 10,986,984, which is a (Continued)

(51) Int. Cl.
*A61B 1/32* (2006.01)
*A61B 1/00* (2006.01)
(Continued)

(52) U.S. Cl.
CPC .......... *A61B 1/00154* (2013.01); *A61B 1/233* (2013.01); *A61B 1/32* (2013.01); *A61B 17/00234* (2013.01); *A61B 17/24* (2013.01); *A61B 17/29* (2013.01); *A61B 17/3415* (2013.01); *A61B 90/00* (2016.02); *A61B 17/3423* (2013.01); *A61B 17/3431* (2013.01); *A61B 90/39* (2016.02); *A61B 2017/00278* (2013.01); *A61B 2017/00849* (2013.01); *A61B 2017/00876* (2013.01); *A61B 2017/2926* (2013.01); *A61B 2017/345* (2013.01); *A61B 2090/08021* (2016.02); *A61B 2090/306* (2016.02); *A61B 2217/005* (2013.01); *A61B 2217/007* (2013.01); *A61M 1/85* (2021.05)

(58) Field of Classification Search
CPC . A61B 1/00147; A61B 1/00154; A61B 1/233; A61B 1/32; A61B 17/3423; A61F 2/82; A61F 2/90
See application file for complete search history.

(56) References Cited

U.S. PATENT DOCUMENTS 5,876,445 A * 3/1999 Andersen ................ A61L 31/04
623/23.7
6,468,301 B1    10/2002 Amplatz et al.
(Continued)

FOREIGN PATENT DOCUMENTS

WO    2015198032 A1    12/2015

*Primary Examiner* — Eduardo C Robert
*Assistant Examiner* — Steven J Cotroneo
(74) *Attorney, Agent, or Firm* — Perkins Coie LLP

(57) ABSTRACT

A surgical sheath adapted for use in the nasal cavity has an elongated hollow body made of a braided material having interstitial spaces with a dimension of 0.25 mm to 1.50 mm. The interstitial spaces filled with a filling material, such as silicone. The sheath has a low profile configuration during placement into the naris, and may be stretched into an expanded configuration. In methods of placing the sheath in the naris, the sheath is folded and then pulled into the naris using a surgical tool.

16 Claims, 25 Drawing Sheets

Related U.S. Application Data continuation-in-part of application No. 15/680,947, filed on Aug. 18, 2017, now abandoned, which is a continuation-in-part of application No. 15/340,718, filed on Nov. 1, 2016, now Pat. No. 9,949,621, which is a continuation of application No. 14/626,184, filed on Feb. 19, 2015, now abandoned, which is a continuation of application No. 13/798,990, filed on Mar. 13, 2013, now Pat. No. 8,986,201.

(60) Provisional application No. 62/396,746, filed on Sep. 19, 2016, provisional application No. 62/377,400, filed on Aug. 19, 2016.

(51) Int. Cl.

| | | |
|---|---|---|
| *A61B 90/00* | (2016.01) | |
| *A61B 17/24* | (2006.01) | |
| *A61B 17/29* | (2006.01) | |
| *A61B 17/00* | (2006.01) | |
| *A61B 17/34* | (2006.01) | |
| *A61B 1/233* | (2006.01) | |
| *A61B 90/30* | (2016.01) | |
| *A61M 1/00* | (2006.01) | |

(56) References Cited

U.S. PATENT DOCUMENTS

| | | | |
|---|---|---|---|
| 9,610,181 B2 * | 4/2017 | Zaver | A61F 2/844 |
| D796,669 S | 9/2017 | Palmer | |
| 10,406,005 B2 * | 9/2019 | Han | A61F 2/90 |
| 10,675,114 B2 | 6/2020 | Ewers et al. | |
| 2004/0116999 A1 * | 6/2004 | Ledergerber | A61F 2/07 |
| | | | 623/1.42 |
| 2005/0090717 A1 * | 4/2005 | Bonadio | A61B 17/0293 |
| | | | 600/208 |
| 2007/0191876 A1 * | 8/2007 | Dubrul | A61M 15/08 |
| | | | 128/207.14 |
| 2009/0082840 A1 * | 3/2009 | Rusk | A61F 2/89 |
| | | | 623/1.11 |
| 2009/0250067 A1 | 10/2009 | Arnon | |
| 2011/0005529 A1 | 1/2011 | Doshi et al. | |
| 2011/0048430 A1 * | 3/2011 | Arnon | A61F 5/56 |
| | | | 131/270 |
| 2011/0118551 A1 * | 5/2011 | Ciporen | A61B 90/00 |
| | | | 600/201 |
| 2011/0172495 A1 | 7/2011 | Armstrong | |
| 2015/0209074 A1 * | 7/2015 | Payne | A61B 17/24 |
| | | | 600/114 |
| 2018/0256146 A1 * | 9/2018 | Chen | A61B 17/0218 |
| 2018/0361129 A1 | 12/2018 | Renner et al. | |

\* cited by examiner

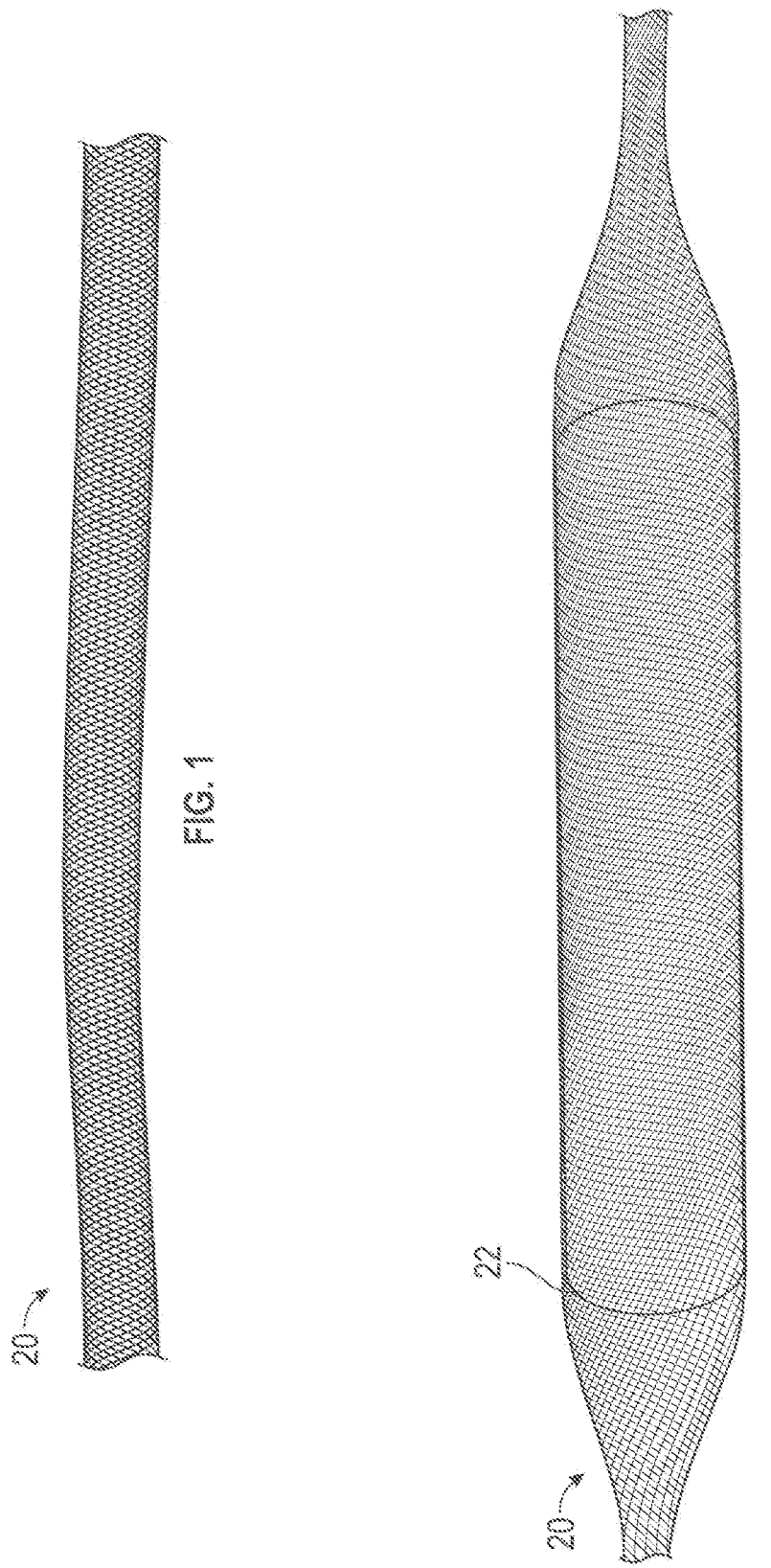

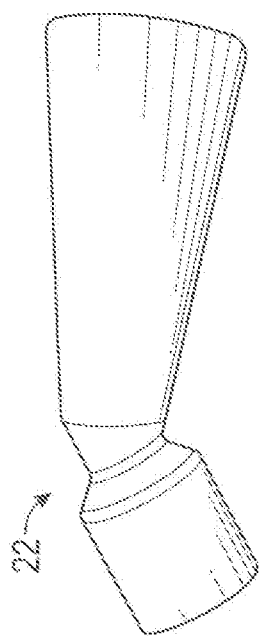
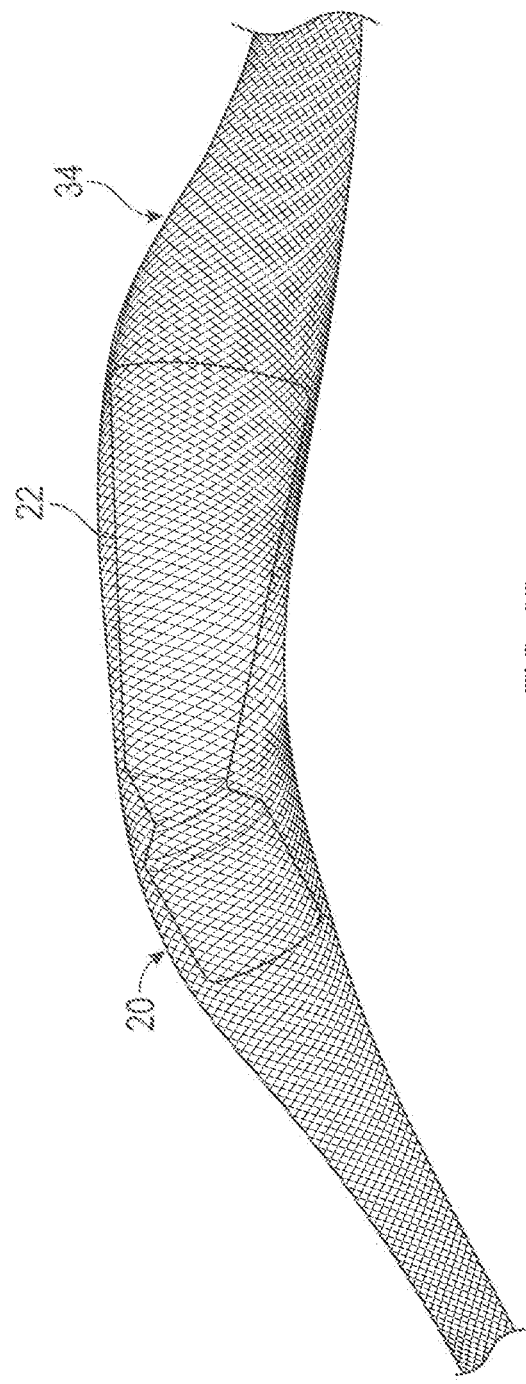

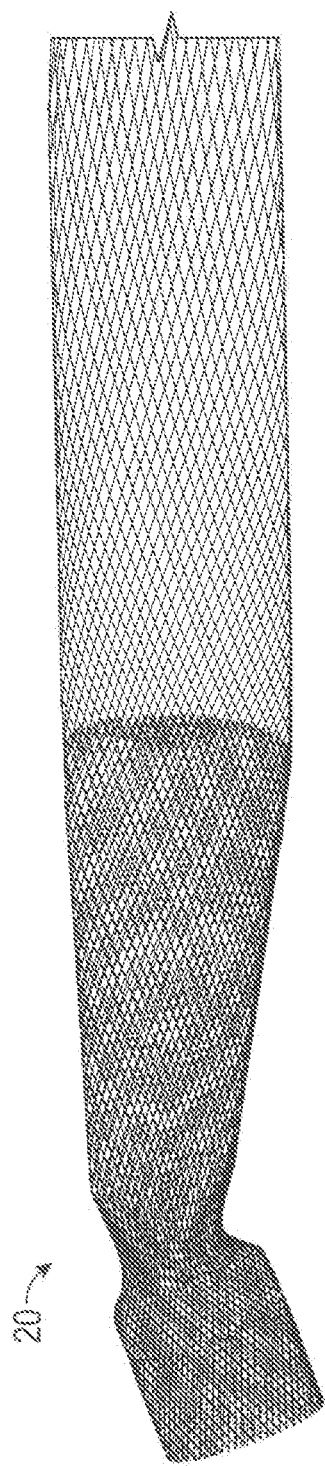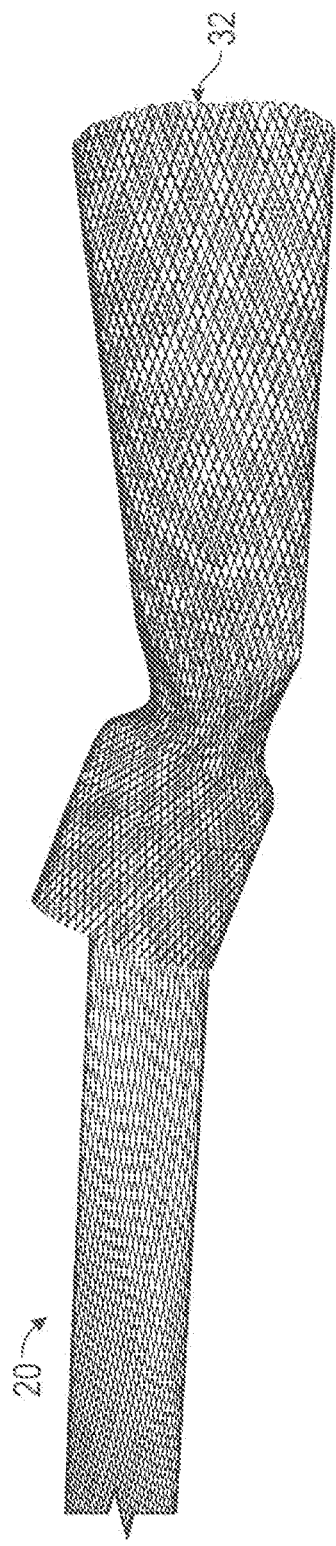

FRICTIONAL PERFORMANCE OVER PROLONGED USE - A HYDROPHICALLY COATED ELASTOMERIC SHEATH VS. AN INHERENTLY LUBRICIOUS COMPOSITE SHEATH

SURGICAL TISSUE PROTECTION SHEATH

This application is a continuation of U.S. patent application Ser. No. 16/211,776, filed Dec. 6, 2018, now pending, which is a continuation-in-part of U.S. patent application Ser. No. 15/680,947 filed Aug. 18, 2017 and now pending, which is a continuation-in-part of U.S. patent application Ser. No. 15/340,718 filed Nov. 1, 2016, now U.S. Pat. No. 9,494,621, which is a continuation of U.S. patent application Ser. No. 14/626,184 filed Feb. 19, 2015 and now abandoned, which is a continuation of U.S. patent application Ser. No. 13/798,990 filed Mar. 13, 2013, now U.S. Pat. No. 8,986,201. U.S. patent application Ser. No. 15/680,947 claims priority to U.S. Provisional Patent Application No. 62/396,746 filed Sep. 19, 2016 and U.S. Provisional Patent Application No. 62/377,400 filed Aug. 19, 2016. Each of the applications listed above is incorporated herein by reference.

BACKGROUND

Endoscopic surgery within the head is a common procedure in neurological surgery and otolaryngology. It avoids large cranial incisions and can reduce the need brain retraction and prolonged wound healing. Endoscopic surgery within the head also provides improved illumination and visualization of the target tissues because the camera of the endoscope is brought directly to the surgical site.

During this type of surgery, there may be local trauma to the tissues in the surgical pathway, resulting from pressure or abrasion caused by the surgical tools. Generally these tissues are the nasal mucosa, turbinates, nasal septum, and sphenoid/frontal/maxillary sinus. When transorbital approaches are used, orbital and periorbital tissue are subject to local trauma. Surgical pathway trauma can add to the trauma of the procedure and prolong the patient's recovery time. Liquids in the surgical pathway, such as mucous, blood, and soiled irrigation fluid, tend to obscure the view of the endoscope. This leads to the constant need for irrigation and suction of the obstructing liquids. In some cases the endoscope may also have to be removed, cleaned and replaced multiple times during a single procedure. This disadvantage tends to increase the complexity and time requirements of the operation. In addition, with each movement of a surgical tool into or out of the surgical pathway, the surrounding tissues are put at risk of additional trauma. Improved devices and methods are therefore needed.

SUMMARY OF THE INVENTION

An access sheath is provided to protect the nasal passageway during endoscopic trans nasal or intra ocular surgery. The access sheath protects the entrance of the naris and sinus from the placement and manipulation of surgical tools both during the initial placement and during manipulation and exchange of surgical tools. The access sheath may provide a guide port to help direct surgical tools into position. In some designs the access sheath may splint the sinus open, to help open and provide access past the turbinate. The access sheath may also help to keep surgical tools and especially an endoscope freer from obscuring matter and secretions The access sheath may be flexible for placement in a folded or rolled up configuration, have a hoop or expansion capability to fill and splint the passage, be partially or totally fluid tight to reduce ingress of secretions, and be lubricious for the unobstructed motion of fine surgical tools during delicate micro surgery.

U.S. Pat. No. 8,986,201 B2 discloses an access sheath, which may be made of elastomer, and has many of the performance features described above. However, elastomer has an inherent draw back. Flexible elastomers are inherently tacky and hence create sliding friction on surgical tools. In some designs this has required additives or a coating on the surface of access sheath to reduce friction. Still generally additives and coatings cannot always provide the surgeon with the feel of a surgical tool sliding against a wet mucus layer.

A nasal access sheath made of a hard plastic material is manufactured in a way to make it flexible, in one embodiment, by using a braided tube. A braid can be made from multiple fibers of plastic monofilament. Monofilaments can be made of rigid and tough plastic such as PET (Polyethylene terephthalate) or Nylon. Monofilaments can even be made from stainless steel. The fibers remain flexible because they have a small diameter, such as 0.08 mm to 0.5 mm. The fibers may have a round cross section, a relatively flat cross section, or elliptical cross section, A plurality of fibers can be braided into a braided tube. As one example, 64 fibers are counter wound in a two over and two under braid. The angle (pics or pitch) of the braided fibers can select the circular profile of the resulting braided tube or sleeve. A braided tube additionally is flexible due to the loose association of the braided fibers and their ability to slide relative to each other but still maintain the intended braided pattern.

BRIEF DESCRIPTION OF THE DRAWINGS

In the drawings, the same reference number indicates the same element in each of the views.

FIG. 1 shows a braided tube.

FIG. 2 shows a braided tube expanded and loaded over a cylindrical mandrel.

FIG. 3A shows a forming mandrel shaped with a geometry for use in the human sinus.

FIG. 3B shows a braided tube expanded and loaded over the forming mandrel of FIG. 3A.

FIG. 7A shows a braided tube created by a single layer of braid formed with a continuation distally of unformed braid. The formed portion was then dipped in a coating of elastomer.

FIG. 7B show the structure of 7A, where the uncoated distal extension of braid has been inverted back through the formed and coated section.

DETAILED DESCRIPTION

FIG. 1 shows a braided tube 20 in its natural braided state. In FIG. 2 the braid is shown on a cylindrical mandrel 22 to demonstrate its tubular shape and ability to expand. The braided tube 20 can be drawn down to a smaller diameter by stretching and pulling the monofilaments into a more longitudinal alignment. Conversely, the braided tube 20 can be expanded to a larger diameter by compression and pushing the filaments into a more radial directed alignment.

The braided tube 20, especially if made of plastic, can be placed around a mandrel 22 that causes the braided tube 20 to expand to a specific diameter or shape. The braided tube 20 can then be heat set in an oven. Upon cooling the braided tube 20 will be permanently formed into the shape of the mandrel 22. Heat setting mandrels can be made of hollow or solid stainless steel, Delrin (acetal homopolymer resin). Mandrels 22 may be made of Teflon (fluoropolymer), especially if intended to coat the braided tube in a plastic/rubber/silicone dispersion. Heat setting can be done at a variety of temperatures and time, depending on the braided tube material and the heat capacity of the mandrel 22. A useful heat set temperature for nylon or PET braids is 120° C. and 150° C. for half an hour, followed by cooling to room temperature in ambient conditions or a quench in water.

FIG. 2 shows braided tube 20 loaded over a Delrin® forming mandrel 22 prior to heat setting. The mandrel 22 may be sized and shaped to product an access sheath having the shape and dimensions discussed in U.S. Pat. No. 8,986, 201, incorporated herein by reference, and as shown in FIGS. 15-22.

FIG. 3A shows a forming mandrel 22 in a geometry for manufacturing an access sheath 40. FIG. 3B shows a braided tube 20 placed over and around the mandrel 22. After the braided tube 20 is loaded over the forming mandrel 22, the braided tube 20 may be conformed to the shape of the mandrel 22 by a partial or complete wrapping of self-adhering silicone tape over the braided tube 20, or alternatively via a shaping block pressed onto the braided tube 20 on the mandrel 22, with the shaping block having an internal opening complimentary to the mandrel, but sized to account for the thickness of the braided tube 20.

Figure 4:
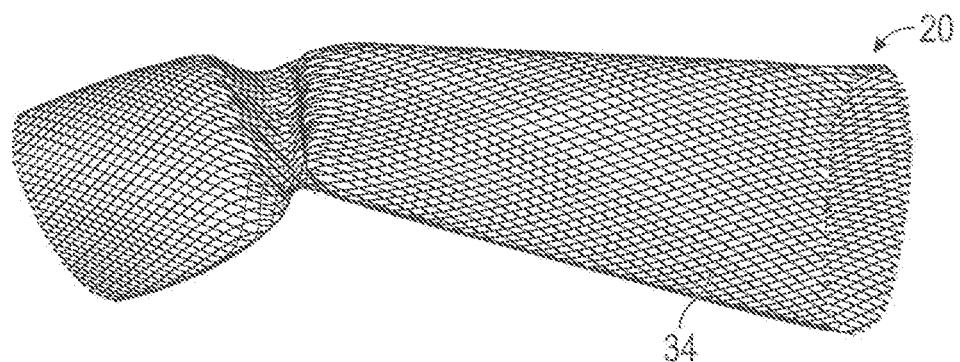
FIG. 4 shows a braided tube that has been heat formed and the mandrel of FIG. 3A removed.

FIG. 4 shows the braided tube 20 after it has been heat formed, removed from the mandrel 22 and trimmed at both distal and proximal ends. This results in a highly flexible, thin, and simple to manufacture access sheath 40. This sheath 40 is permeable which allows natural mucus lubrication of the sinus to enter into the access sheath for additional lubricity. The braiding pattern may be modified to allow more or less permeability by changing the diameter of fibers or filaments of the braid material. Flat monofilament or multi-filar fibers may be used to increase the PIC (how tight the braiding is formed), and reduce the interstitial spacing between fibers of the braided tube 20.

The braided tube 20 may be coated with a semipermeable or more preferably an impermeable membrane. A less tacky coating or a harder urethane material, of durometer 50 A or harder, may be used. It can be applied in thicknesses of 0.1 mm to 0.3 mm. Due to the thinness and the flexibility of the braided tube, even when coated the braided tube may still remain flexible, foldable, and be able to elongate.

In an alternate embodiment a PET (Polyethylene Terephthalate) braided tube can be used with a uniform coat of a silicone dispersion (Nusil MED16-6606). Despite being silicone this combination provides a slick surface relative to surgical tools. This can be attributed to the mechanical nature of the structure. The braid surface provides a non-continuous, undulating surface where a full surface contact is replaced by a series of discrete contact points. Discrete contact points reduce the surface area of contact and hence reduce the friction between access sheath 40 and the surgical tool.

A single layer braided tube coated in an impermeable silicone, such as NUSIL silicone dispersion 6061, was found to be a good coating as it applies in a thin layer and despite being silicone (that has inherent tackiness) has little tack. The resulting friction as tested showed 50 grams of friction. This is about the same friction as hydrophilic coated devices when tested new. The lubricious nature of the material also does not degrade over time, unlike hydrophilic coatings.

Examples of lubricious coatings are: ceramic coatings. Slick-Sil coating (by Surface Solutions Group), Parylene coating, and hydrophilic coatings. Similar coatings can provide better friction reduction but may not feel as lubricious as mucous membrane.

Hydrophilic coating provide lubricity similar to mucous membranes, however they require wetting with water or saline to activate, and need periodic or continuous re-wetting to stay slick. Hydrophilic coatings also wear away after multiple abrasions with surgical tools and may not withstand the long procedure time of skull base neurosurgery. Examples of lubricious additives are: barium sulfate, powdered Teflon (fluoropolymer) glass fillers, and ceramic fillers. These can reduce the surface tack but also tend to provide a surgical tool feel that is different from mucous membranes.

The elastomeric coating on the internal surface of the braided tube 20 may be reduced. If the mandrel 22 is created from a semi flexible rubber or jacketed in rubber it results in a flexible surface. If the braided tube 20 is loaded over this surface and stretched to tightly engage the mandrel 22, the internal contact points of the braided tube embed slightly into the semi-flexible mandrel surface. This effectively masks the internal surface of the braid. A coating step fully coats the external braided tube while leaving the highest contact points of the internal braided tube uncoated and fully retaining the inherent lubricity of the hard plastic monofilament of the braided tube. A semi flexible surface may also be achieved by jacketing the mandrel in polyolefin shrink tubing. When the braid/jacket mandrel are heated for shaping, the shrink tubing softens and the braided tube will slightly embed. This similarly creates a braid/mandrel assembly that has a partially masked inner braid surface for a follow up coating step.

Figure 5:
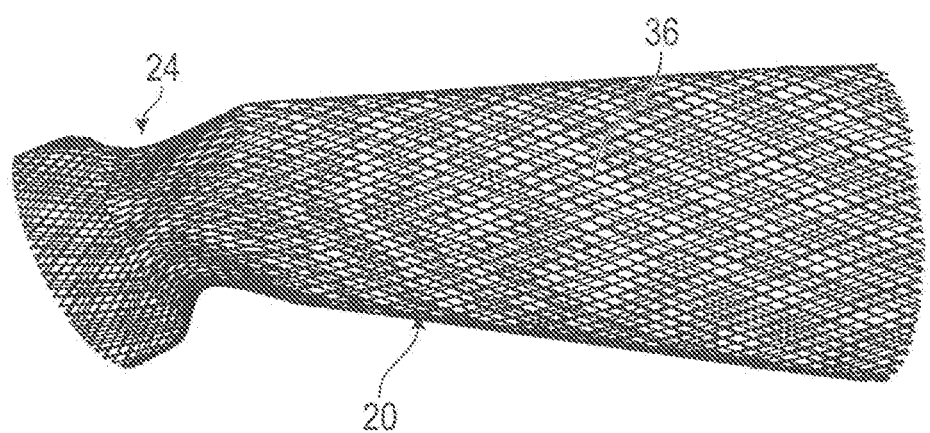
FIG. 5 shows a heat formed braided tube that has been coated with an elastomer.

FIG. 5 shows a formed braided tube that has been coated in the silicone dispersion described above. The distal end may be made atraumatic for insertion in the delicate anatomy of the nasal cavity, for example by using a double layer 36 of the braided tube material, in contrast to the single layer 34 shown in FIG. 4. The double layer 36 may be provided by inverting the braided tube 20 to create a dual wall braided tube with an un-cut, rolled or rounded edge 32.

Figure 6:
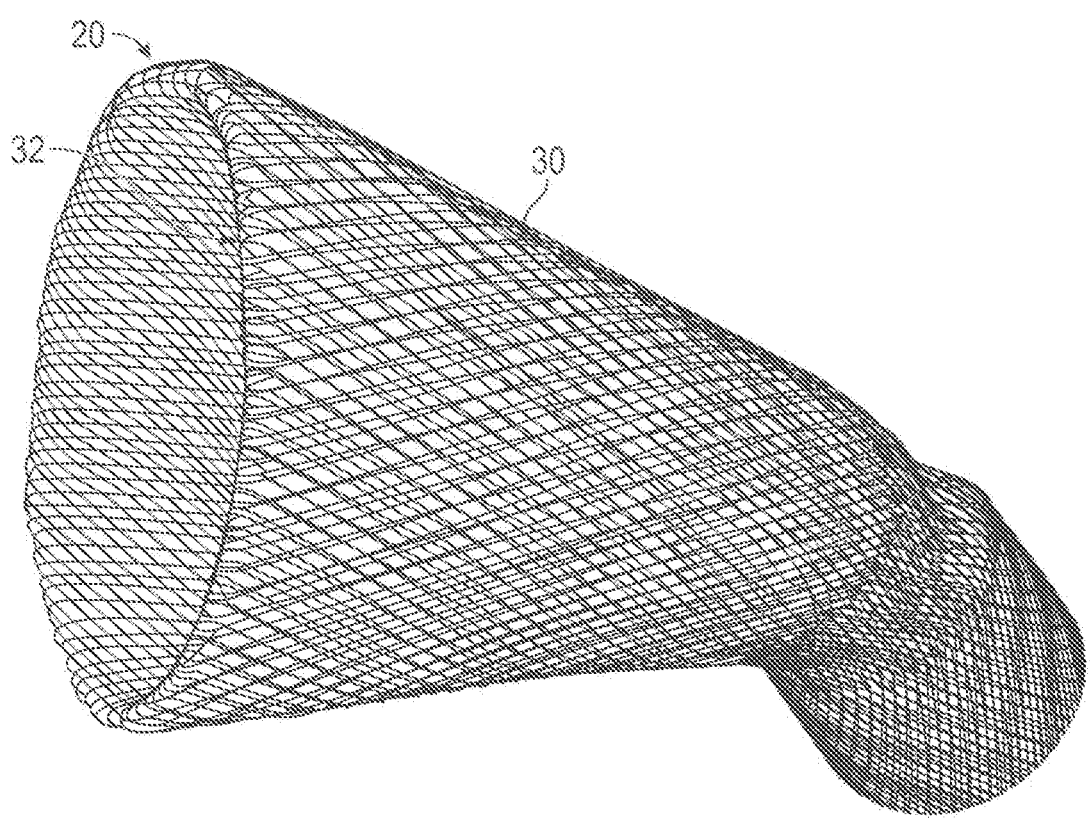
FIG. 6 shows a heat formed braided tube with the braid inverted to form a dual layer, and with the distal end folded back on itself to provide a rounded tip.

FIG. 6 shows a formed braided tube 20 having an inverted braid section 30 to create the rounded edge 32. The rounded edge 32 can be dipped completely into a coating. This creates an impermeable surface in a simple way, although it may reduce flexibility or the ability to draw down and fold since both braid layers are bonded together.

Figure 7C:
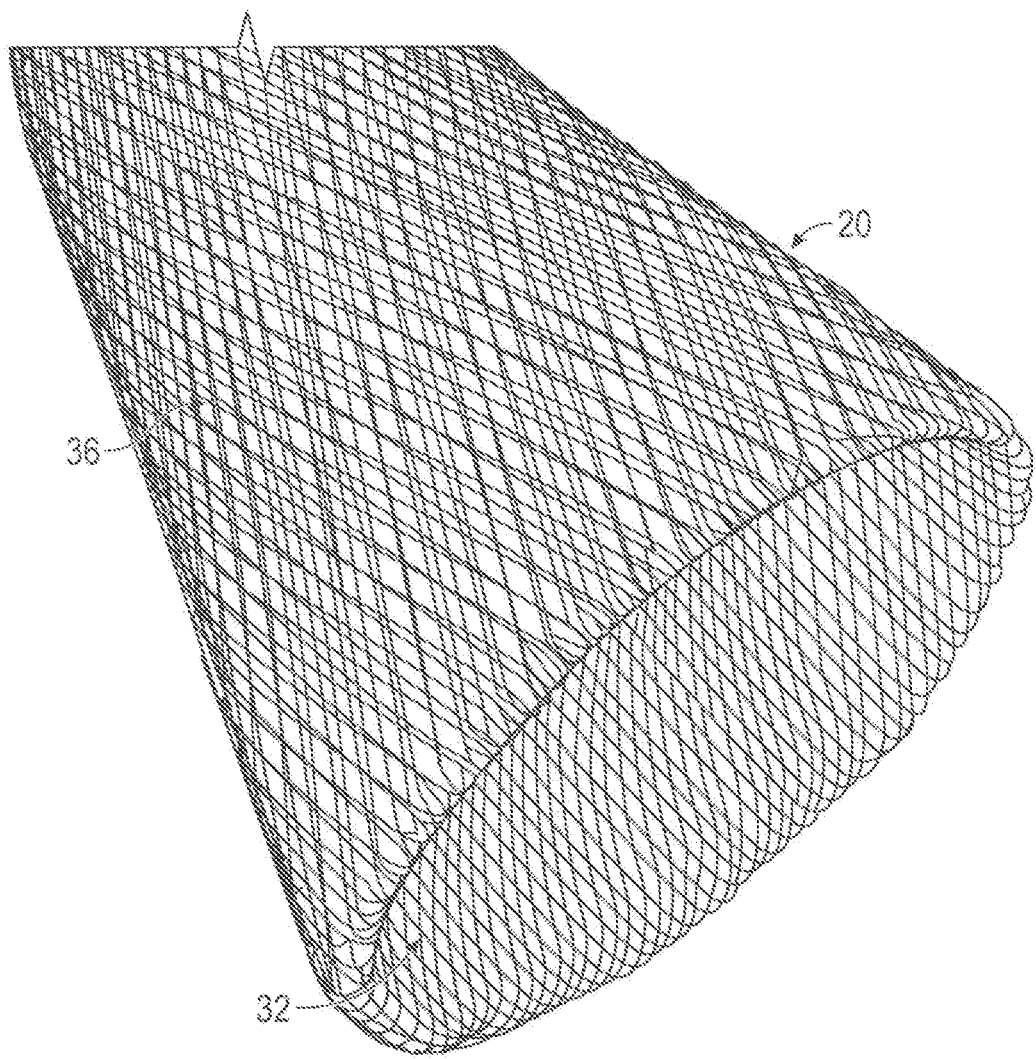
FIG. 7C shows the structure of FIG. 7A where the uncoated distal extension of braid was then inverted resulting in a braided tube having a rounded distal end and an un-coated inner surface and a coated outer section.

FIGS. 7A-7C show an alternative to the rounded edge design of FIG. 6, with the benefit of the rounded edge 32 has no coating on the inner surface, while the outer surface is coated, and does not bond the layers together preserving a thinner wall and flexibility.

Figure 8B:
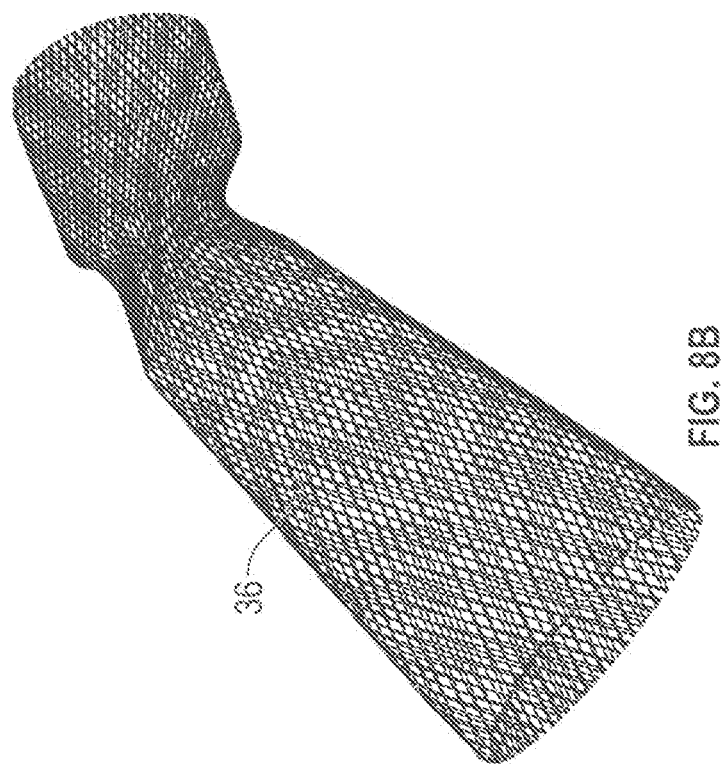
FIG. 8B shows the distal end of a two layer braided tube with an inverted distal end.
Figure 8A:
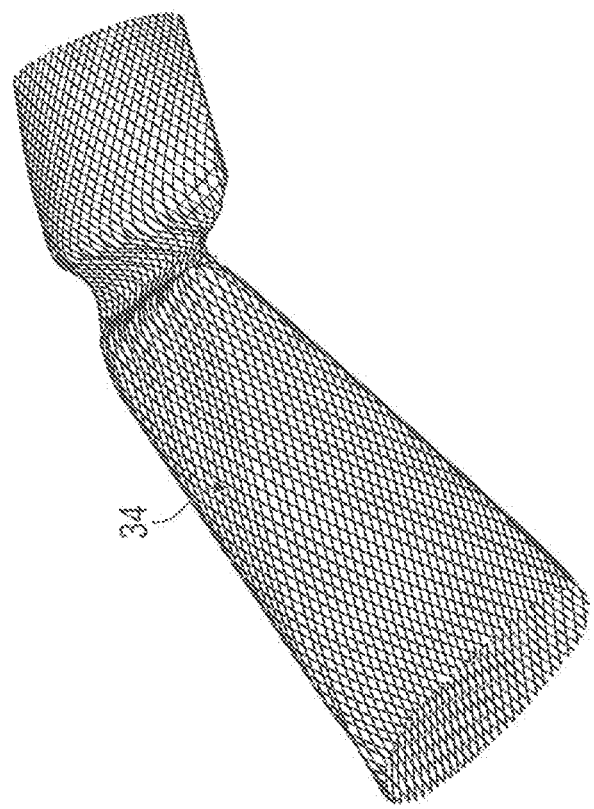
FIG. 8A shows the distal end or edge of a single layer braided tube.

Referring now to FIG. 7A, the right side of the braided tube 20 is formed on a mandrel 22 and then coated. The left side is not formed or coated. Referring now to FIG. 7B, the uncoated braid (left side) is inverted and loaded through the shaped and coated right side portion. Referring now to FIG. 7C, the rounded edge 32 (formed via the inverting step) and the coated external surface and uncoated internal surface are shown. For comparison, FIG. 8A shows an access sheath with a straight edge while FIG. 8B shows an access sheath 40 with a rounded edge 32.

As is apparent from the description of FIGS. 3-8B above, a method of making a surgical access sheath may include placing a length of braided tube material over a mandrel; conforming the braided tube material to the shape of the mandrel; heating the braided tube material to heat set the braided tube material; removing the braided tube material from the mandrel; and cutting the heat set braided tube material to a desired length. The conforming step can be performed by at least partially wrapping tape over the braided tube material, or placing a shaping block having an internal opening complimentary to the mandrel, over the braided tube material.

A monofilament material having round or flat fibers may be used as the braided tube material. A sheet or strip of braid material may also be used in place of a tube, with the sheet or strip formed into a tube during the manufacturing process. For example, a strip of braid material may be wrapped around the mandrel and formed into a tube via the heat setting. A coating may be applied to at least part of the heat set braided tube.

Internal contact points of the braided tube material may optionally be embedded into the mandrel surface, and a coating applied onto at least part of the heat set braided material. One or both ends of the heat set braided material may be folded or rolled to form an atraumatic end.

Figure 9A:
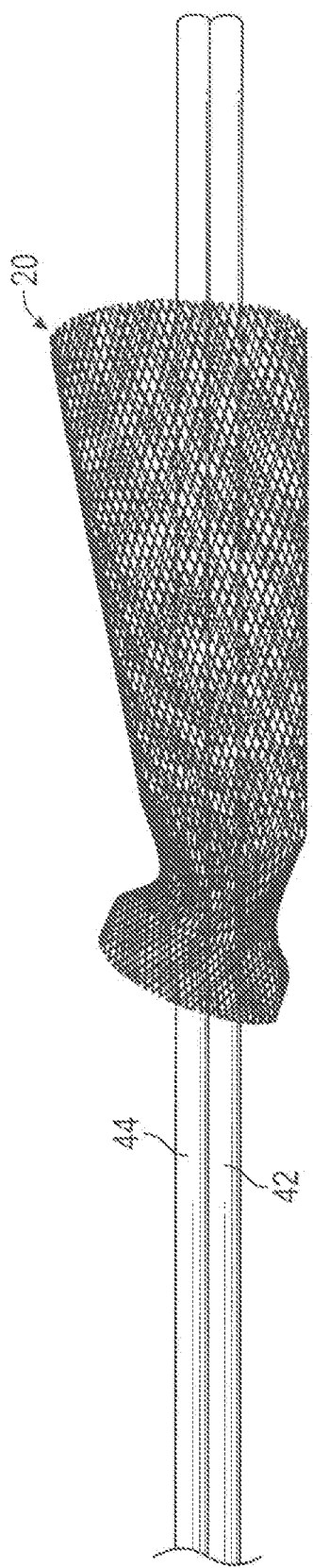
FIG. 9A shows the coated braided tube of FIG. 7C or 8B with two surgical tools placed in parallel.
Figure 9B:
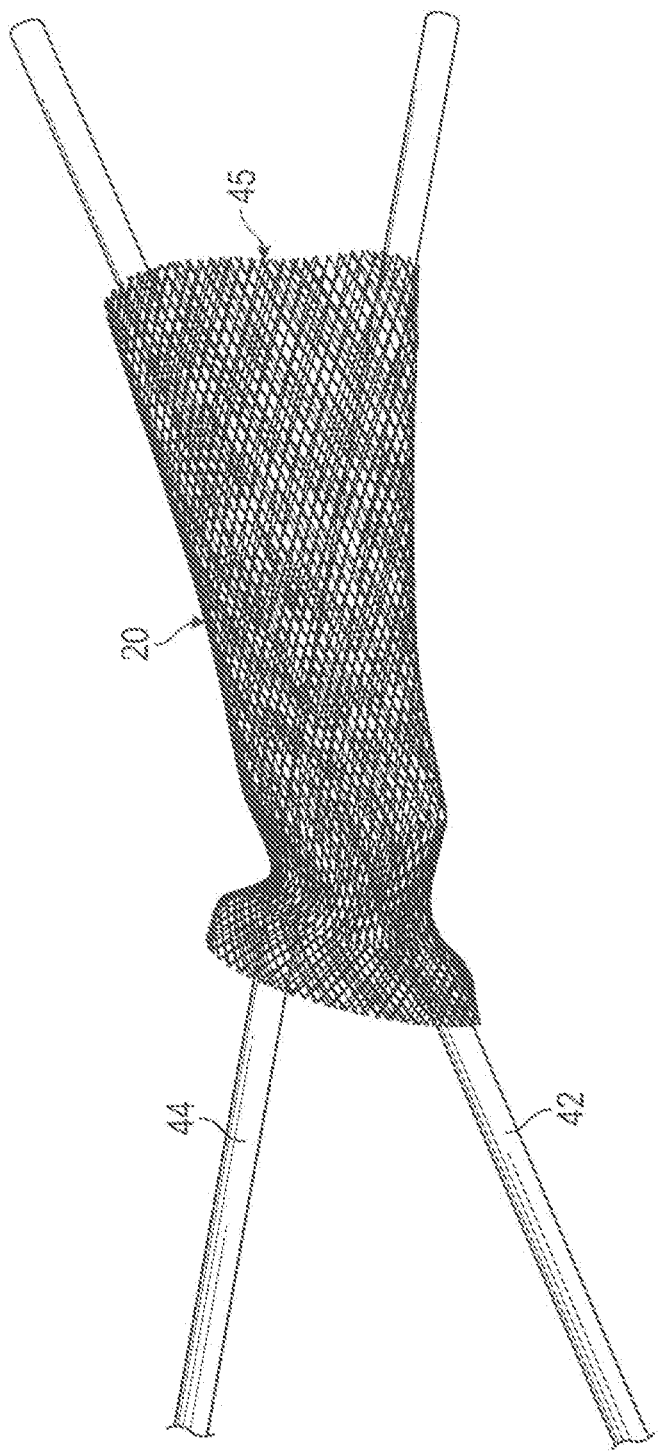
FIG. 9B shows the coated braided tube with two surgical tools at an acute angle and the flexible response of the neck of the structure.

FIGS. 9A and 9B show a finished access sheath 40, and demonstrate its ability to conform to significant angulation of surgical tools 42 and 44. The access sheath 40 can stretch as shown in FIG. 9B when surgical tools are angulated and apply a spreading load on the access sheath 40. In typical endonasal skull base procedures, multiple surgical tools are used to stretch the naris in order to increase the angle formed by two surgical tools creating a triangulation rather than bringing the distal ends of the surgical tools together. The access sheath 40 can preferably stretch as much as or more than the tissue of the naris. The access sheath 40 can accommodate the varied anatomy of the human nares and stretch and contract to accommodate surgical tool requirements.

The access sheath 40 may be compressed or folded for low profile placement and high profile working position. In a simple case the access sheath can be folded by hand and slid into the sinus manually. Loading tools or kits may also be used.

Figure 10A:
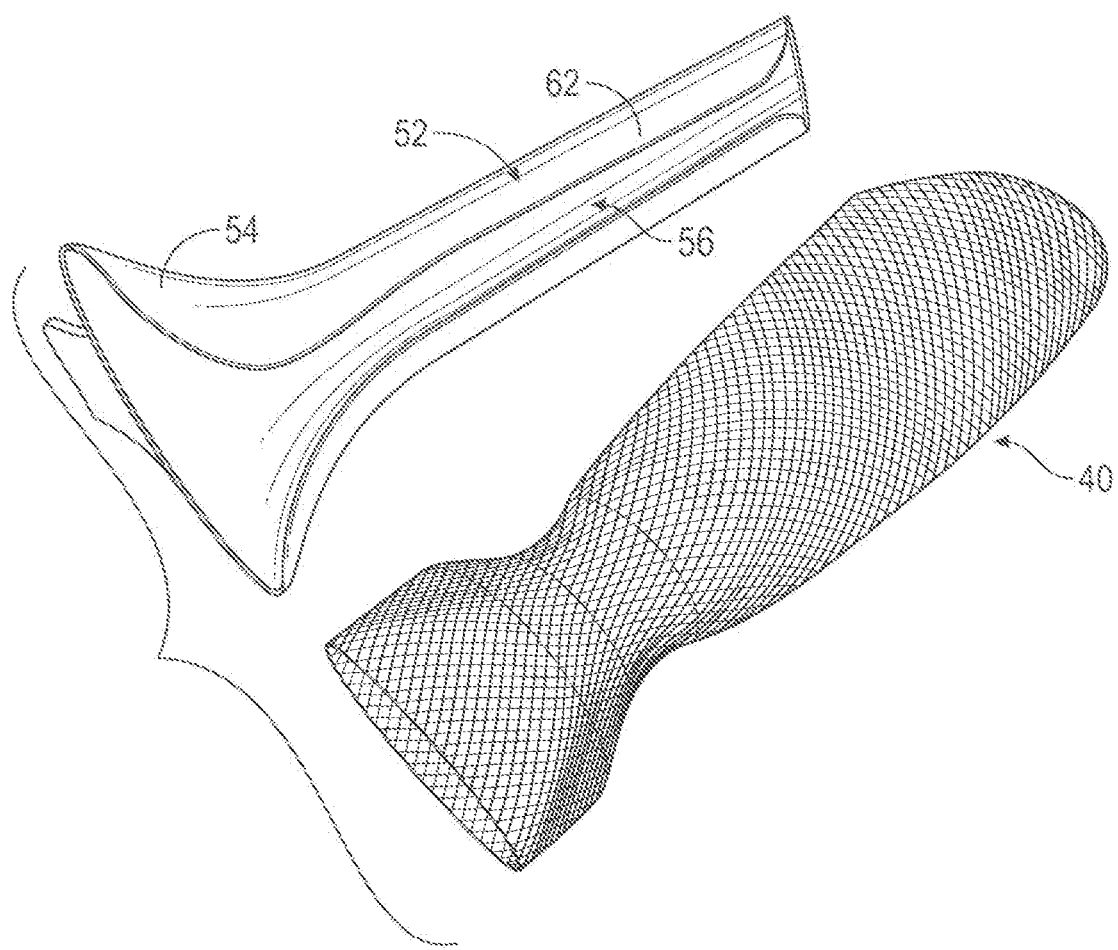
FIG. 10A shows the coated braided tube next two an introduction tool that has a longitudinal release slot.
Figure 10B:
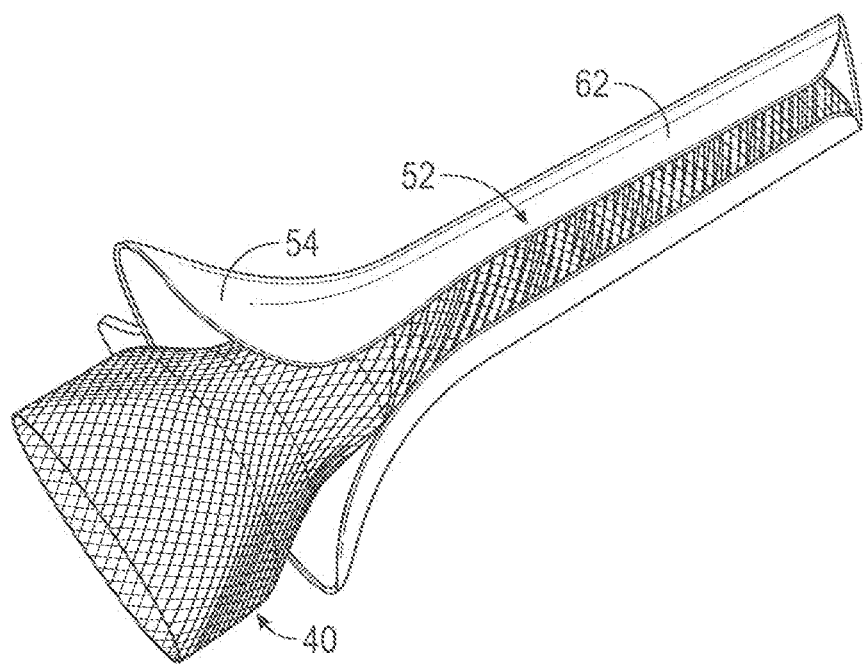
FIG. 10B shows the coated braided tube loaded into the introduction tool of FIG. 10A.
Figure 10C:
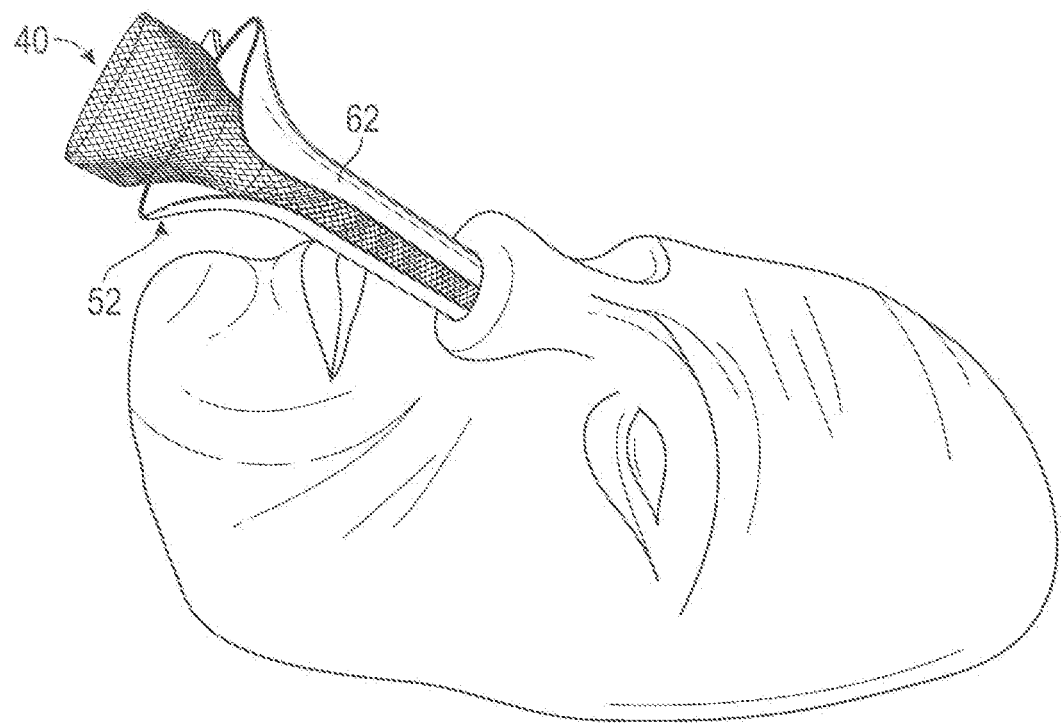
FIG. 10C shows the loaded introduction tool being inserted into the nose.
Figure 10D:
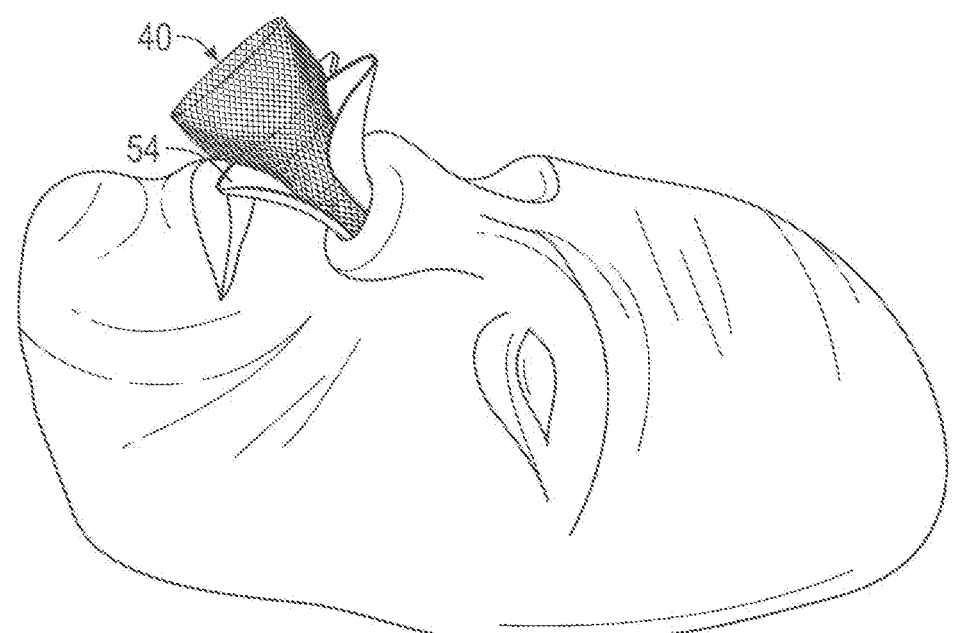
FIG. 10D shows the introduction tool fully inserted into the nose.
Figure 10E:
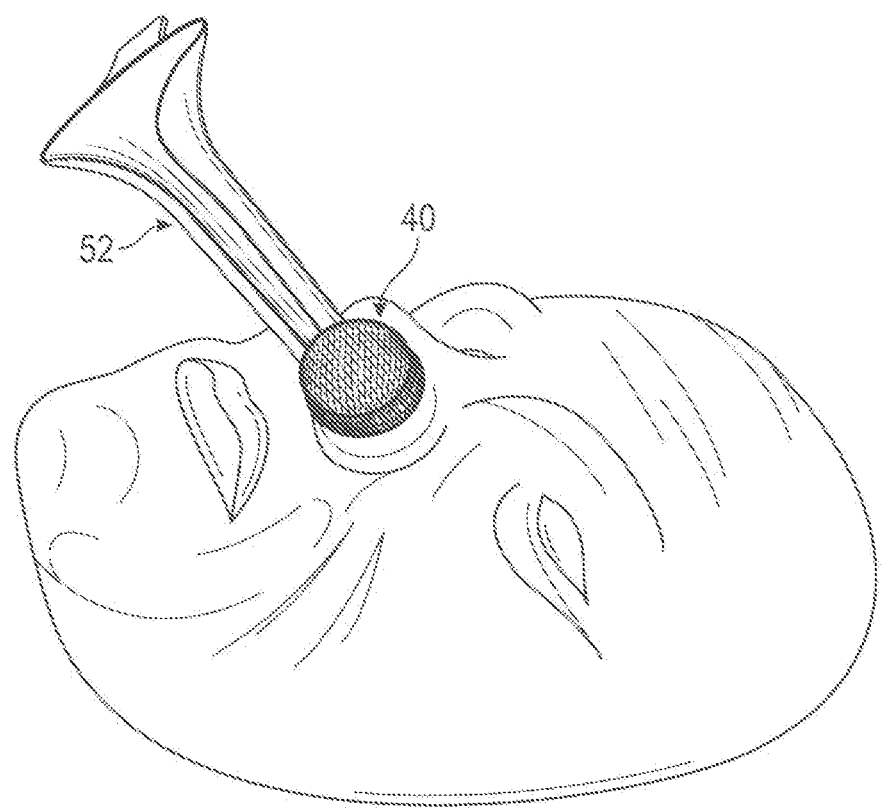
FIG. 10E shows the coated braided tube being mostly released out of the longitudinal release slot of the introduction tool.
Figure 10F:
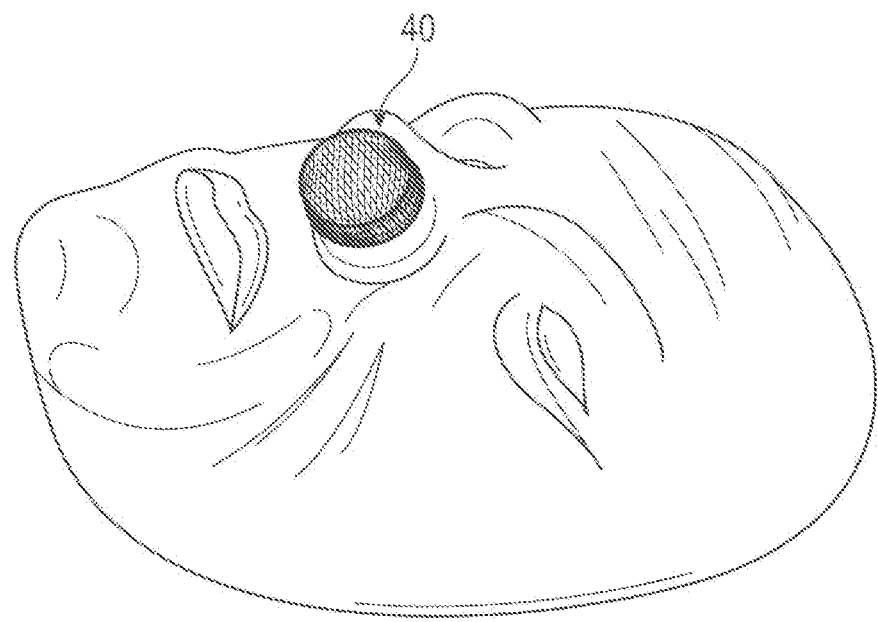
FIG. 10F shows the coated braided tube fully released out of the longitudinal release slot.

FIG. 10A-10G show a system or kit 50 for low-profile insertion of the access sheath 40. FIG. 10A shows the access sheath 40 next to an elongated tubular loading tool 52. The loading tool 52 has a flared proximal end 54 to aid in channeling the access sheath 40 into the elongated tubular body 62 of the loading tool 52. The loading tool 52 has a slot 56 along one side to allow the access sheath 40 to be separated from the loading tool after it is placed in the nose of the patient. FIG. 10B-10F show the placement of the access sheath 40. The access sheath 40 can be loaded via the loading tool 52 to 1) Compress and control the access sheath 40 into a compact volume; 2) provide a streamlined low profile shape for inserting the access sheath 40 into the narrow space of the nasal opening and cavity; and/or 3) provide a conduit for deploying the access sheath 40.

The loading tool 52 has a flared proximal end 54 to allow the access sheath 40 to be easily inserted into the loading tool 52 and compacted into a small volume. A tubular body 62 is joined to the flared proximal end 54 of the loading tool 52. The tubular body 62, which may be straight or have a slight taper towards the distal end, is designed to fit into the nasal opening. The slot 56 along the side of the loading tool 52 provides a conduit for the access sheath 40 to be deployed and released.

The kit in FIGS. 10A-10G may be provided with an access sheath 40 comprising a braid material, and a loading tool 52 having a conical proximal end, and a tubular distal end, and the slot 56 extending along one side of the loading tool, along the entire length of the loading tool. The loading tool comprises a flexible material to allow the slot to be pushed open further, to better allow the sheath to moved out of the loading tool into the nose or other body cavity. The slot has a width equal to 25% to 45% of a minimum diameter of the tubular distal end.

Figure 11A:
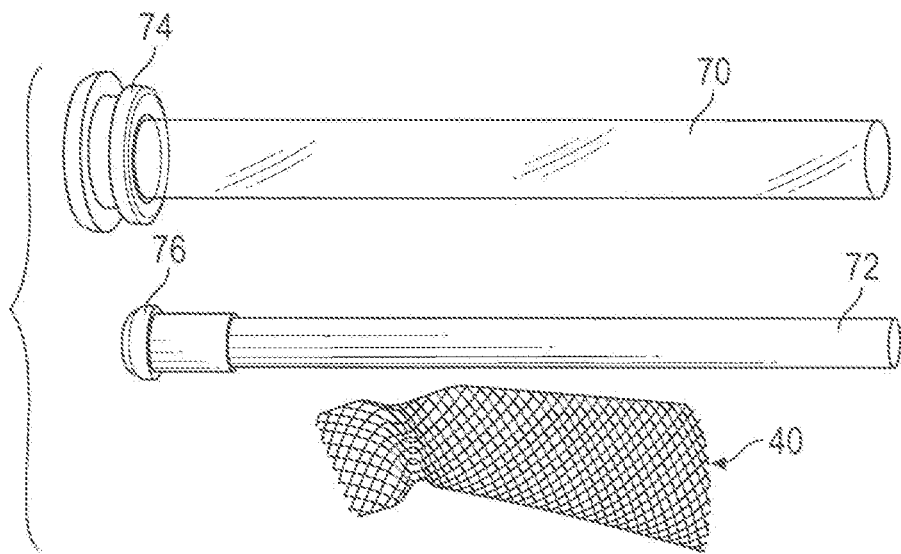
FIG. 11A shows the access sheath and a plunger deployment tool.
Figure 11B:
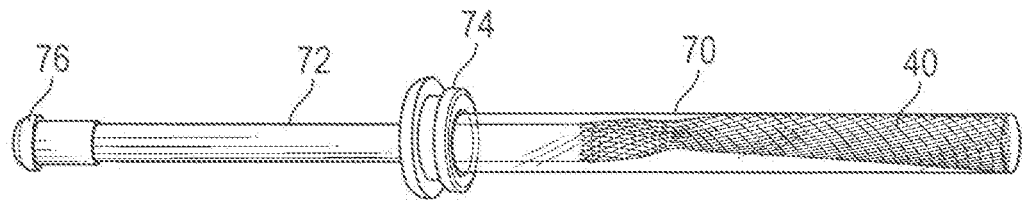
FIG. 11B shows the access sheath loaded in the plunger deployment tool.
Figure 11C:
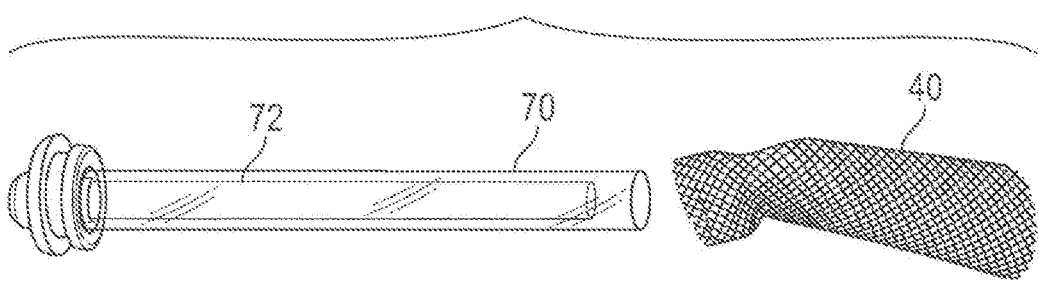
FIG. 11C shows the access sheath expelled distally from the plunger deployment tool.

Turning to FIG. 11A, in an alternative access sheath kit, the access sheath 40 may optionally be folded and slid into a tube 70. The tube 70 may be a thin walled round or oval tube, optionally with an annular collar 74 at the back or proximal end to provide a grasping surface. The folded or rolled access sheath 40 may be inserted into the distal or proximal end of the tube. The plunger 72 is inserted into the proximal end as shown in FIG. 11B. The tube 70 is then introduced into the nose. Advancing the plunger while holding the tube stationery pushes the access sheath 40 out of the distal end of the tube as shown in FIG. 11C. The tube and plunger may then be withdrawn by pulling back on the tube, leaving the access sheath 40 in place in the nose. The plunger 72 may have an enlarged head 76 having a diameter greater than the collar 74 or the tube 70, to limit the extent of travel of the plunger into the tube.

As shown in FIGS. 11A-11C, the surgical kit has an access sheath 40 made of a braided material, and a loading tool set including the tube 70 and the plunger 72 slidable into the tube. The access sheath 40 is foldable or compressible to fit into the tube, and with the access sheath expandable when ejected from the tube by the plunger. The tube may have an outside diameter of 5 to 20 mm and be transparent or translucent.

Figure 12A:
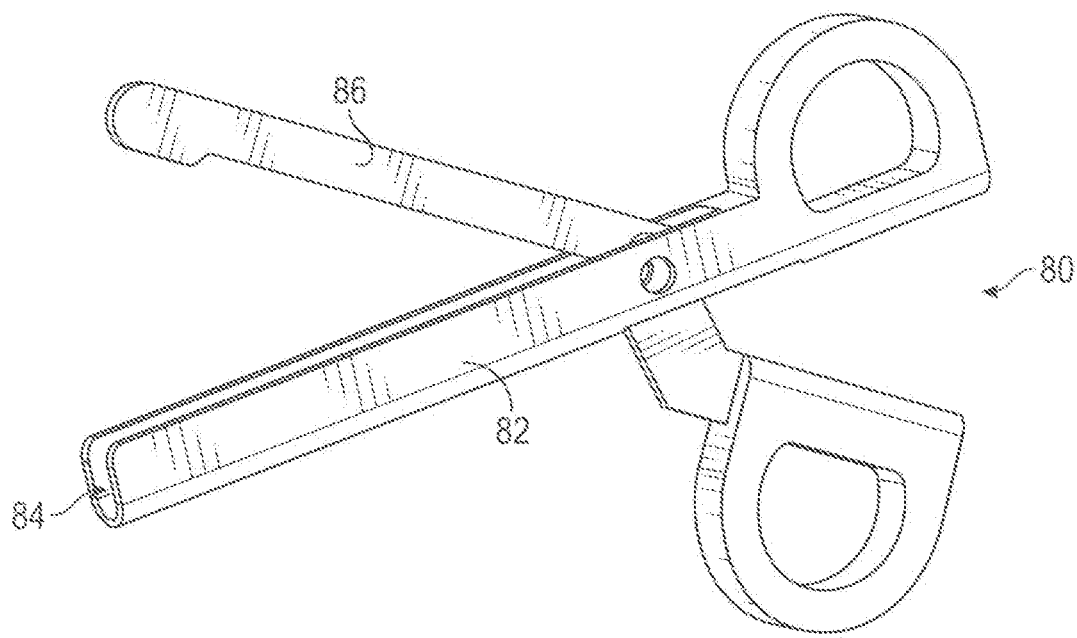
FIG. 12A shows a beam and groove scissor-like delivery tool in an open position.
Figure 12B:
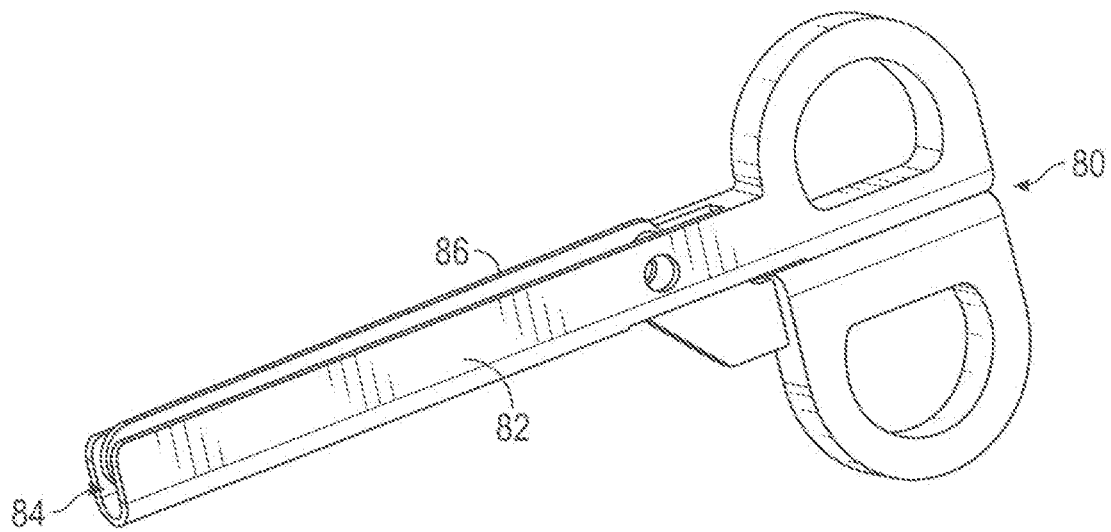
FIG. 12B shows the delivery tool of FIG. 12A in a closed position.
Figure 12C:
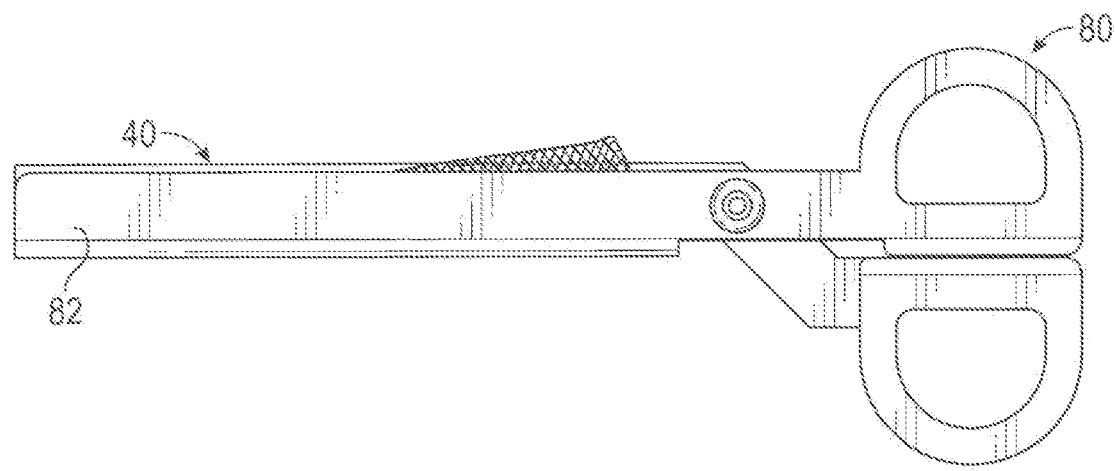
FIG. 12C is a top view of the access sheath of FIG. 5, 8A or 9 loaded onto the delivery tool.
Figure 12D:
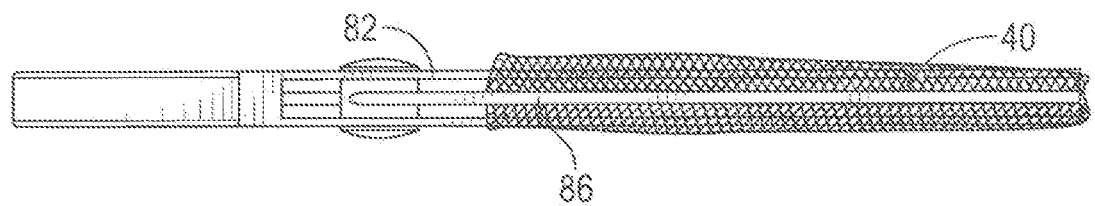
FIG. 12D is a side view of the access sheath and delivery tool shown in FIG. 12C.

FIG. 12A to 12C show another kit using a folding instrument 80 to fold, introduce and deploy the access sheath 40. The folding instrument 80 is a scissor-like device having a bottom jaw 82 having an elongated grooved channel 84. The top jaw 86 is an elongated rod or beam pivotally attached to the bottom jaw 82, with a handle at the back end of each jaw.

In use the instrument 80 is opened, as shown in FIG. 12A and the access sheath 40 is placed between the open jaws 82 and 86, or over one of the jaws. Squeezing the handles towards each other pivots the jaws towards a closed position shown in FIG. 12B, with the access sheath folded between the jaws. The jaws are then inserted into the nasal cavity and opened slightly to release the access sheath. The instrument 80 is removed while the access sheath 40 is left in place. The instrument 80 can be re-inserted into the internal channel 45 of the access sheath 40 and then manipulated open and closed to help open and expand the access sheath as needed.

The designs of FIGS. 12A-12C if provided as a surgical kit, includes the access sheath 40 made of a braid material, and the scissor-like loading tool having the first jaw pivotally attached to the second jaw, with the first jaw having a channel and the second jaw movable at least partially into the channel when the scissor-like loading tool is in a closed position, to fold the access sheath.

Figure 13A:
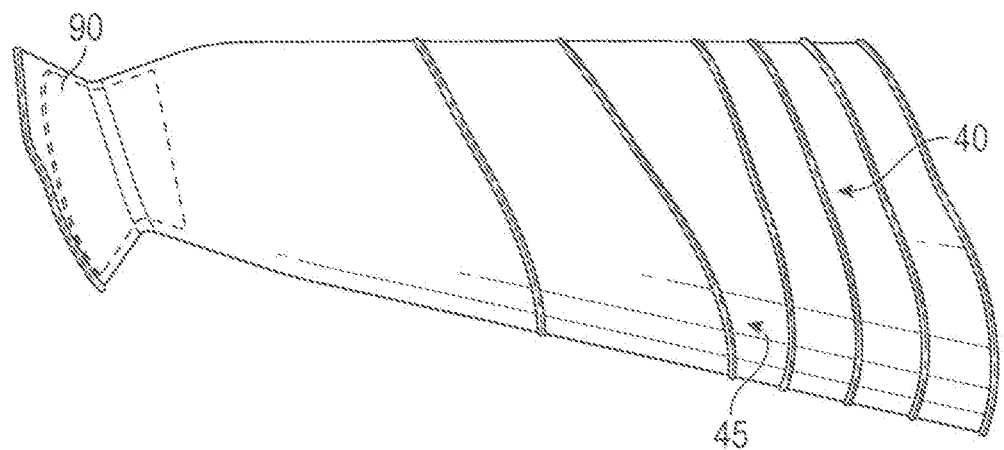
FIG. 13A is a side view of an embodiment of an elastomeric access sheath having a rigid plastic internal collar to create a low friction surface.
Figure 13B:
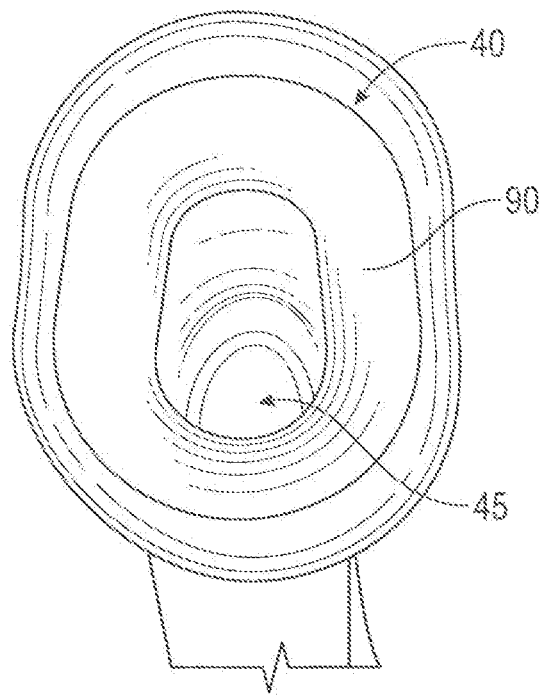
FIG. 13B is a front end view of the access sheath shown in FIG. 13A.
Figure 13C:
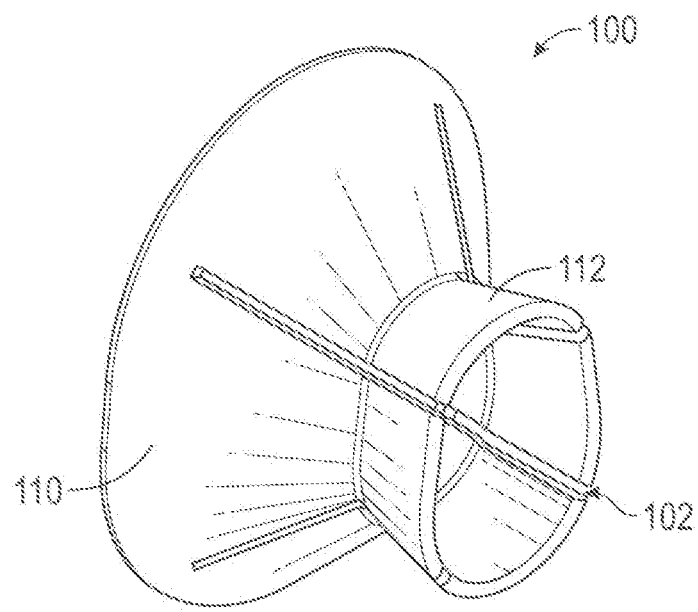
FIG. 13C shows a rigid collar for installment in an access sheath, with the rigid collar having radial slots to allow the rigid collar to flex.

Referring to FIGS. 13A and 13B, a conical collar insert 90 may be placed in the angle section 154 and flare section 156 of the access sheath 40, shown in FIGS. 15-22. The insert 90 may be made from a hard plastic or metal so that it is inherently lubricious relative to metal or plastic surgical tools 44. The insert 90 provides a lubricious bearing surface at the angle and flare sections of the access sheath 40, where surgical tools 44 extensively contact with the access sheath 40.

Figure 13D:
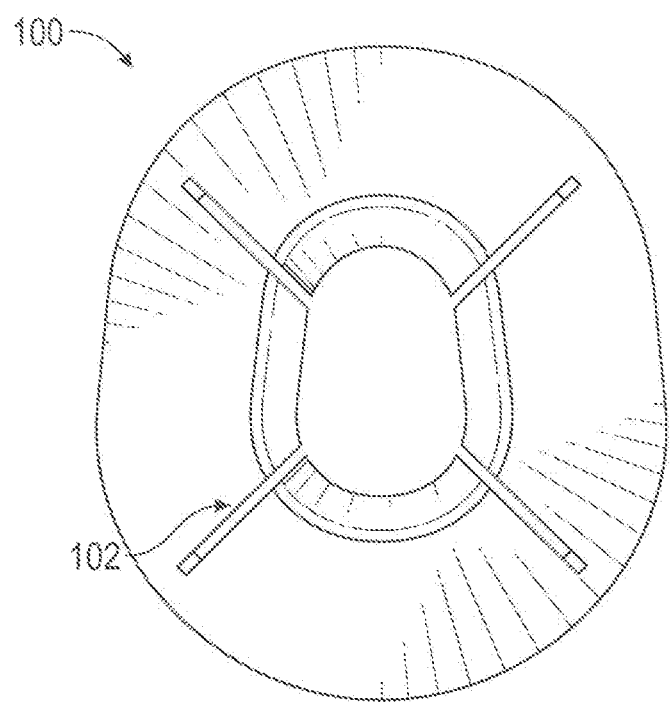
FIG. 13D shows the rigid collar of FIG. 13C installed in an access sheath.
Figure 13E:
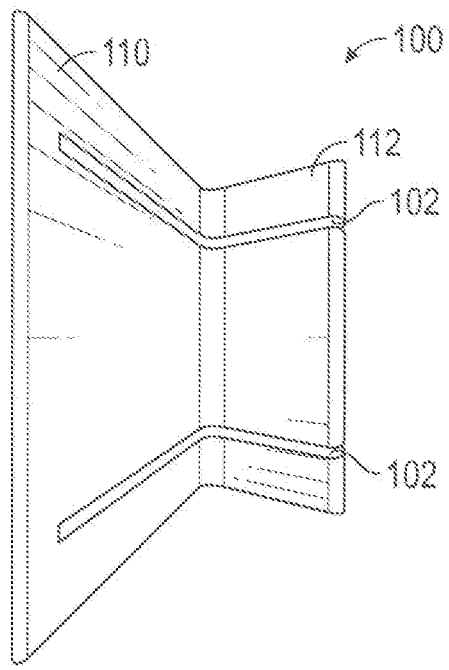
FIG. 13E is a side view of the rigid collar shown in FIG. 13C.
Figure 13F:
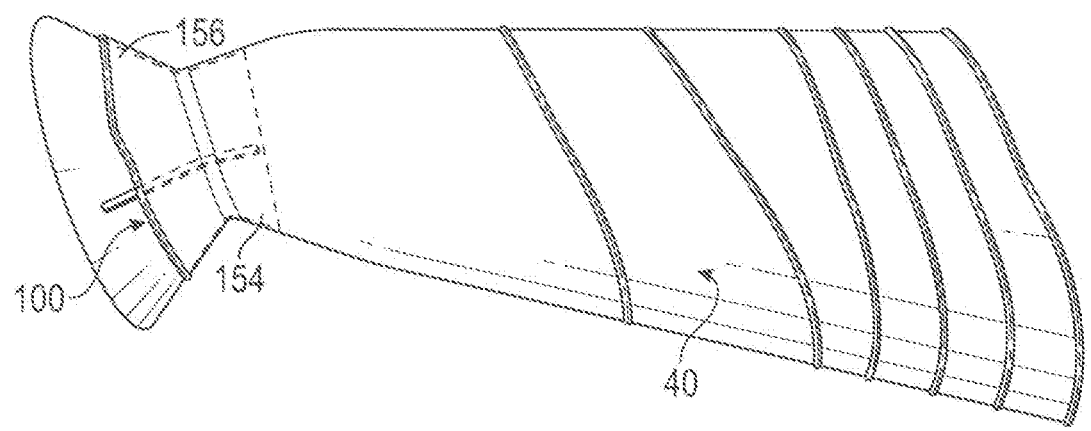
FIG. 13F is a side view of an embodiment of an elastomeric access sheath having the rigid plastic internal collar shown in FIG. 13C.

FIGS. 13B to 13E show an alternative conical collar insert 100 which is a rigid collar having radial slots 102 to allow it to flex into a more open state in response to forces exerted by surgical tools 44. This allows the surgical tools 44 to be more easily moved into larger acute angles relative to each other. The collar inserts 90 and 100 may each have a flared section 110 joined to a tubular section 112 having straight or parallel walls. Alternatively the tubular section 112 may have a reverse flare wherein it tapers outwardly towards the distal end. As shown in FIGS. 13A and 13D, the flared section 110 has a shape and dimensions to allow it to fit and be attached into the flare section 156 of the access sheath 40. The tubular section 112 is similarly configured to fit into the angle section 154 of the access sheath 40. The inserts 90 and 100 may be attached to the access sheath 40 via adhesive, plastics welding, shrink fit, molded into place, snap fit, etc.

Figure 14:
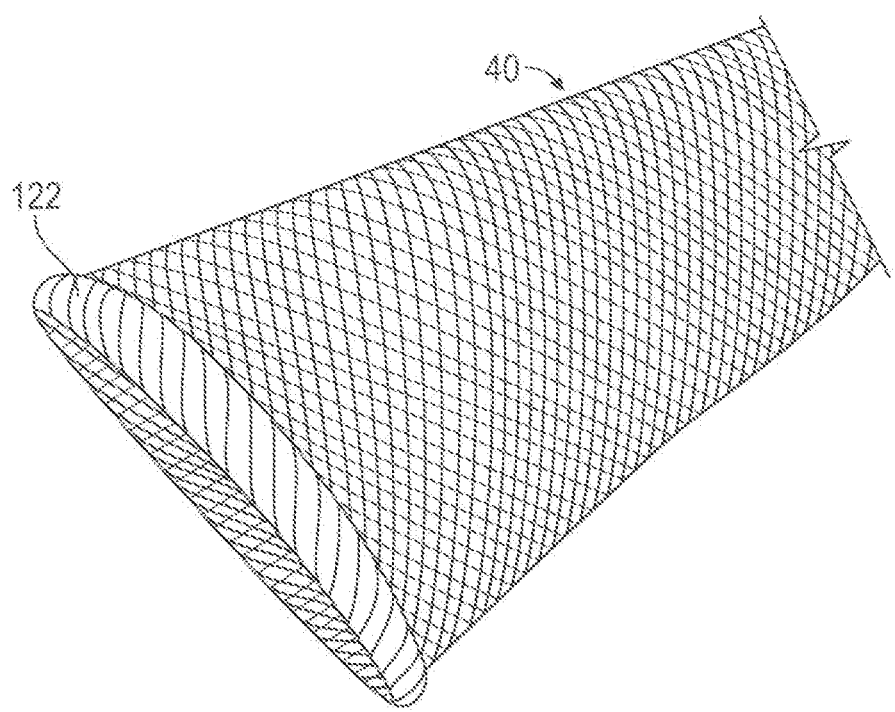
FIG. 14 shows the access sheath with an external rim of elastomer to create an atraumatic tip.

FIG. 14 shows an access sheath 40 with a distal end 120 of an elastomer to create an atraumatic tip 122. The elastomer can be an internal and external rim. Preferably the elastomer is only on the external surface so as not to create an internal surface of elastomer. This provides an atraumatic tip 122 but does not create an internal elastomeric surface that could result in a friction inducing surface at the distal end of the internal channel 45 of the access sheath 40. The elastomer may be provided a cut edge of a single layer of braided tube material, or over the rounded edge 32 of a access sheath 40 having two layers of braided tube material at the edge.

The elastomer may extend proximally 1-50 mm on the external surface of the access sheath 40. The external extended elastomeric surface 124 provides a user selectable section that may be cut to a desired length. When cut, a portion of the external extended elastomeric surface 124 remains on the access sheath 40 and provides an atraumatic distal rim. An external rim of elastomer may similarly be used on the proximal end of the access sheath. This provides a section at the proximal end that maintains the integrity of the braided tube and avoid fraying. The external rim of elastomer on the proximal rim, if used, may only be on the external surface so as not to create friction on surgical tools passing through the internal channel 45.

Figure 16:
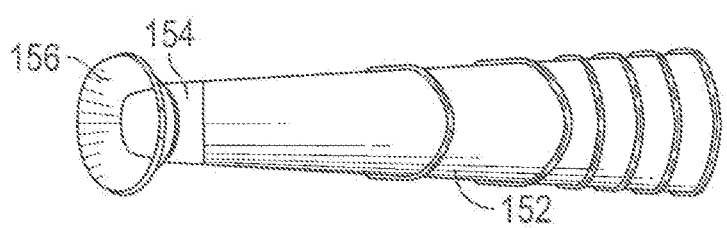
FIG. 16 is a bottom view of the sheath shown in FIG. 15.
Figure 17:
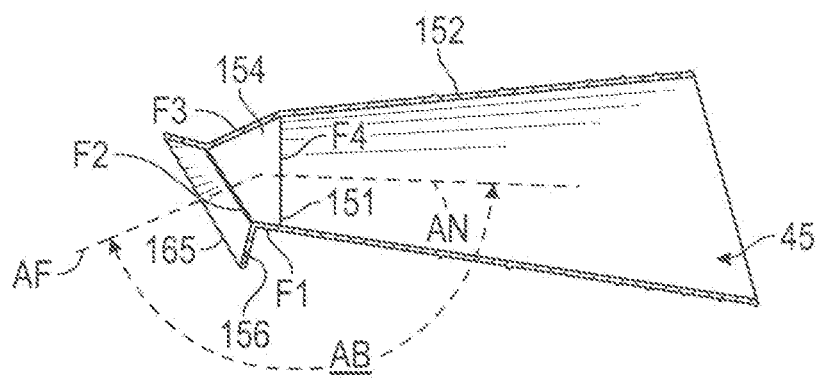
FIG. 17 is a section view of the sheath shown in FIG. 15.
Figure 18:
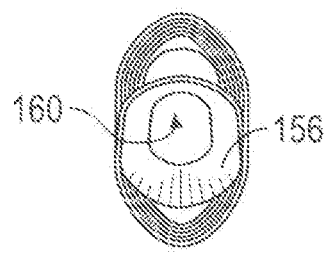
FIG. 18 is left end view of the sheath of FIG. 15.
Figure 19:
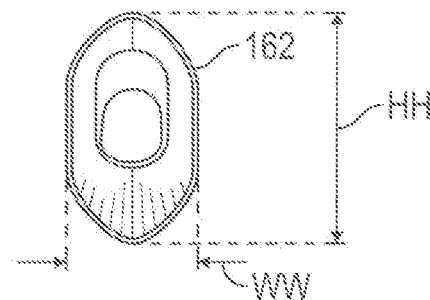
FIG. 19 is a right end view of the sheath of FIG. 15.
Figure 20:
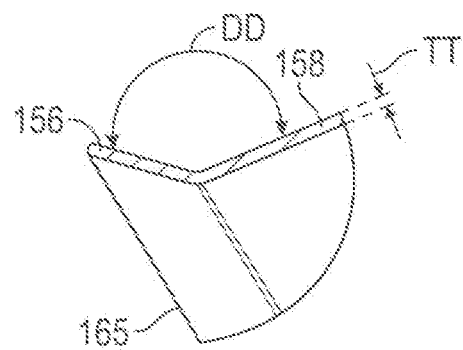
FIG. 20 is an enlarged detail view of detail A shown in FIG. 18.
Figure 21:
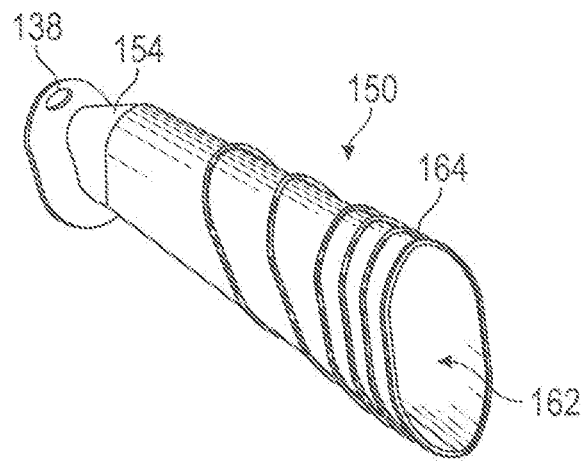
FIG. 21 is front, top and right side perspective view of the sheath shown in FIG. 15.
Figure 22:
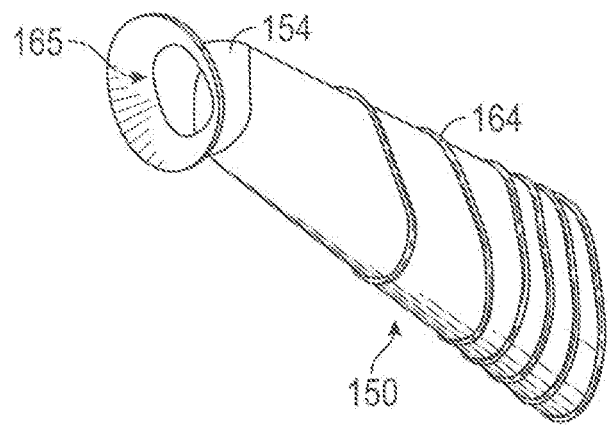
FIG. 22 is rear, bottom and right side perspective view of the sheath shown in FIG. 15.

FIGS. 15-22 show dimensions and angles which may be used for the access sheath 40. The mandrel 22 may be sized and shaped to form an access sheath as shown in these Figures. In this example, the access sheath 40 has a body section 152, and angle section 154 and a flare or conical section 156. The sheath 40 may be formed of braid material as a one piece unit with the body section 152, the angle section 154 and the flare section 156 integrally joined together. As shown in FIG. 20, the sheath 40 may have a thin flexible wall 158 having a thickness TT which allows the sheath to conform to the body orifice, or the inner wall of the patient's nostrils in the case of nasal access. The flare section 156 may be provided as a conical ring forming an angle DD of 120-160 or 130-150 degrees with the top wall of the angle section. The sheath 40 may have a single through internal channel 45 extending from a distal opening 162 to a proximal opening 165. As shown in FIGS. 18, 19 and 22, the openings 162 and 165, and the cross section of the body section 152, may be generally in the shape of an oval or an ellipse.

Figure 15:
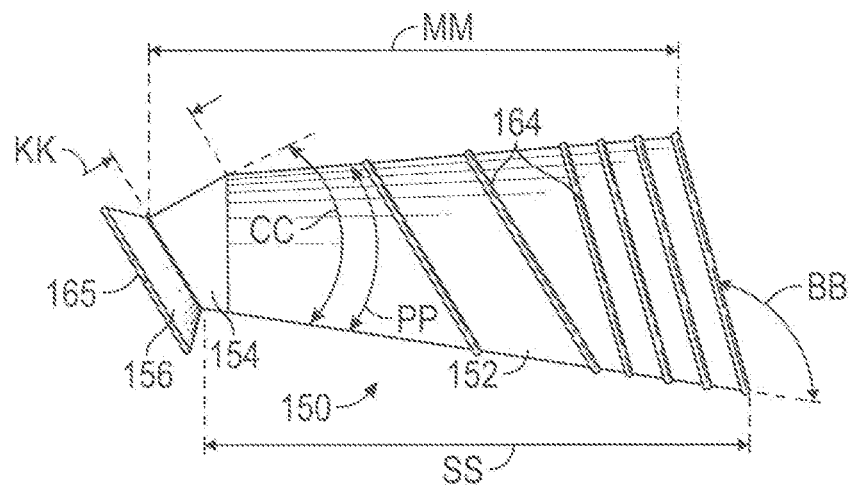
FIG. 15 is a side view of the access sheath of FIGS. 3-9B with preferred dimensions and angles.

Referring to FIGS. 15 and 17, the distal opening 162 may lie in a plane forming an angle forming an angle BB with the bottom of the sheath 40, with BB ranging from 95 to 125 or 100 to 115 degrees. As best shown in FIG. 17, the angle section 154 may be described as joined to the body section 152 at a vertical line 151. The upper and lower walls of the sheath extend distally away from the vertical line 151 towards the distal opening 162 at acute angles to the vertical line 151, which may the same or different angles. As shown in FIG. 15, the included angle CC between the top surface of the angle section 154 and the lower wall of the body section may range from 25 to 40 or 30 to 35 degrees. The angle PP in FIG. 15 relating to the diverging angle of the top and bottom surfaces of the body section is typically 10-20 or 12-16 degrees. Dimension KK may be 8-16 or 10-14 mm, with dimensions MM and SS both generally about 65-85 or 70-80 mm.

As shown in FIGS. 15-17, a surgical sheath 40 includes a conical section; an angle section joined to the conical section, with the conical section having a central axis AF not parallel to a central axis AN of the angle section; a body section joined to the angle section, with the body section having a length at least twice the length of the angle section; and the conical section, the angle section and the body section comprising a braid material. The sheath 40 may further include an insert 90, 100 inside of the conical section, with the insert made of a non-braid material. An elastomer coating may be provided on at least part of an external surface of the sheath. The sheath may have a rolled edge at its distal end.

Turning to FIGS. 15-16 and 20-22, one or more ridges 64 may be provided on an outer surface of the body section 152. The ridges may optionally be provided as rings extending continuously around the outside surface of the body section. The dimensions and angles shown in the drawings of all embodiments may typically be varied by 10, 20 or 30% depending on various design parameters.

The angle section 154 may allow the proximal end of the sheath 40 to be more easily stretched and/or deflected. This allows for more versatile movement of surgical tools extending through the sheath during surgery. As shown in FIGS. 15 and 17 the angle section 154 forms an irregular quadrilateral shape in cross section. In FIG. 17 the angle section 154 may be defined by line F4 along with segments or lines F1, F2 and F3, with F4 and F2 forming a first acute angle and with F1 and F3 forming a second acute angle. Each of the sides or segments F4, F1, F2 and F3 forming the angle section 154 may also have different lengths. F3 may be substantially perpendicular to F2. The angle section 154 may alternatively be described via a centerline AN perpendicular to and bisecting segment or line F4 and intersecting a centerline AF of the flare section 156 at an angle AB of 5-30 or 10-20 degrees.

One method for placing a surgical access sheath includes loading a surgical access sheath into a loading tool, with the surgical access sheath comprising a braid material, and with the loading tool having a conical proximal end, and a tubular distal end, and a slot extending from the conical proximal end to the tubular distal end; inserting the loading tool into a body orifice; inserting a surgical tool into an internal channel of the surgical access sheath; moving the surgical tool to move the surgical access sheath out of the loading tool through the slot; and withdrawing the loading tool from the body orifice.

Another method for placing a surgical access sheath includes placing a surgical access sheath into a low profile delivery position, with the surgical access sheath comprising a braid material; loading the surgical access sheath into a tube; inserting the loading tool into a body orifice; moving a plunger into the tube to eject the surgical access sheath out of the tube and into the body orifice; and withdrawing the tube from the body orifice.

Another method for placing a surgical access sheath includes providing a scissor-like loading tool having a first jaw pivotally attached to a second jaw, with the first jaw having a channel and the second jaw movable at least partially into the channel when the scissor-like loading tool is in a closed position; providing a surgical access sheath comprising a braid material, with the access sheath having an internal channel; placing the access sheath around one of the first jaw and the second jaw, while the jaws are in an open position; moving the jaws into the closed position, to fold and grasp the surgical access sheath; inserting the jaws into a body orifice; opening the jaws to release the surgical access sheath; and removing the jaws from the body orifice.

A surgical kit includes an access sheath comprising a braid material; and a loading tool having a conical proximal end, and a tubular distal end, and a slot extending from the conical proximal end to the tubular distal end. The loading tool may comprise a flexible material. Typically the slot extends along an entire length of the loading tool. The slot may have a width equal to 25% to 45% of a minimum diameter of the tubular distal end. The access sheath may have a conical section, an angle section joined to the conical section, with the conical section having a central axis AF not parallel to a central axis AN of the angle section, a body section joined to the angle section, with the body section having a length at least twice the length of the angle section. Alternatively, the loading tool may have a tube and a plunger slidable into the tube, with the access sheath foldable or compressible to fit into the tube, and with the access sheath expandable when ejected from the tube by the plunger. If used, the tube may have an outside diameter of 5 to 20 mm, and it may be transparent or translucent. A scissor-like loading tool may also be used, with the scissor-like loading tool having a first jaw pivotally attached to a second jaw, with the first jaw having a channel and the second jaw movable at least partially into the channel when the scissor-like loading tool is in a closed position, to fold the access sheath.

Surgical instruments must be able to pass across the surface of the braided structure with minimal friction and without catching on the braid or the interstitial space between the braid elements. For the structure to be useful it must be comprised of a tight, dense, braid pattern with minimal interstitial space.

Figure 23:
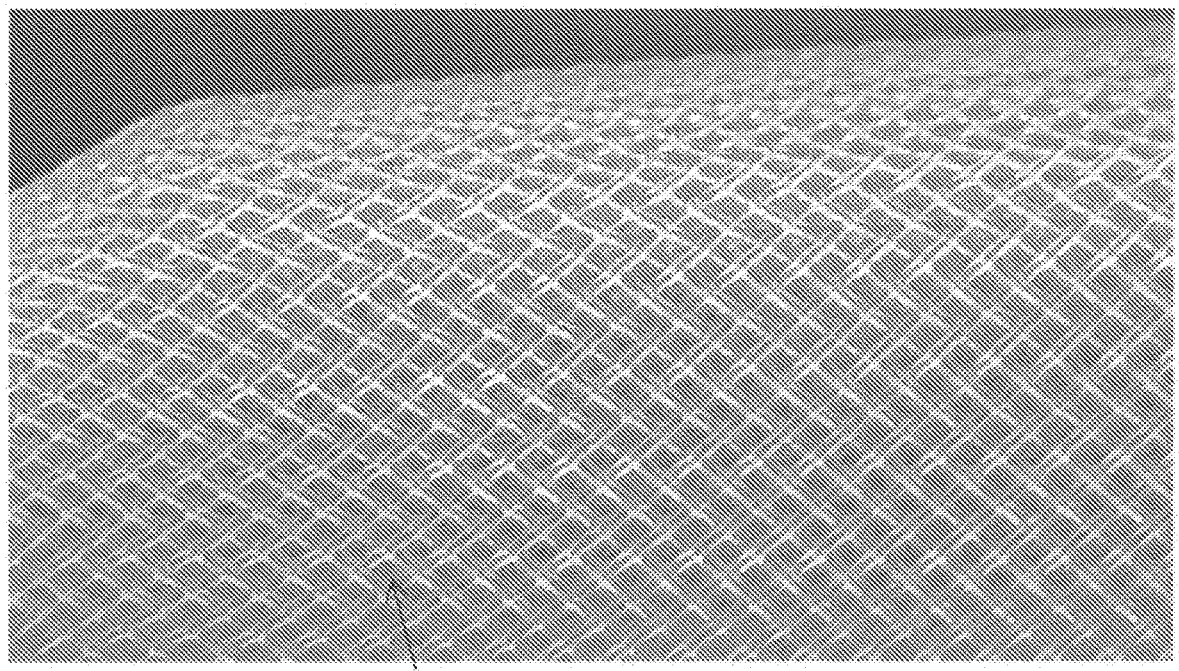
FIG. 23 is an enlarged perspective view of a surface of a composite surgical sheath made of a braided material with a sealing material in the interstitial spaces of the braided material.

FIG. 23 is a magnified image of a braided access sheath. Interstitial spaces are formed between the adjacent and intersecting fibers forming the braid material. In FIG. 23, the interstitial spaces are generally square. Depending on the overall curvature of the sheath, and on the directions applied forces in compression or tension, the interstitial spaces may have other quadrilateral shapes, including isosceles trapezoid, rhombus or diamond, parallelogram and kite (i.e., rhombus with two adjoining longer sides and two adjoining shorter sides).

The shapes of the interstitial spaces may change during use as the braided material stretches or compresses. As used here, an interstitial space is defined as an equilateral quadrilateral with a dimension represented by the length of one side, in the as manufactured shape without any forces acting on the sheath.

The braid material of the access sheath may have interstitial spaces with a dimension of between 0.50 mm (0.020 in.) to 0.75 mm (0.030 in.), or 0.25 mm (0.010 in.) to 1.50 mm (0.060 in.)

Minimizing the interstitial space is significant because a small interstitial space between the braid elements creates a weave which is difficult for tools to snag on or poke through. A small interstitial space between the braid fibers also allows a coating of a filling or water proofing material, such as silicone (polysiloxane) to span the interstitial space. The larger the interstitial spaces, the more difficult it is for the coating to maintain coverage across the spaces. Spaces not fully covered, or filled in, with a coating create voids or pinholes which may tend to cause the tip of a tool to catch or snag in the braid material. Materials such as silicone may be used for the filling or water proofing material, including polymers, natural and synthetic rubbers, and elastomers generally. These may be applied to the braided material by dipping, spraying, rolling, etc. The filling material fills in the interstitial spaces, and may or may not also form a layer thickness above the braided material, on the inside and/or the outside surface of the sheath.

If the interstitial space is too small, it may create issues in manufacture and use of the sheath, as the braid sheath material in effect approaches becoming a solid material. Additionally, some interstitial space allows a coating to access and encapsulate the braid fibers. Without interstitial space the coating would only be able to form a surface film. A surface film may be prone to delamination with compression, stretch, or tool passage and create a higher friction coefficient. Additionally, there is a frictional benefit from having a surface that in not continuous. The discontinuous surface formed by the fibers of the mesh material reduce the surface area in contact with tools and directly reduces static and dynamic friction acting on the tools. For these reasons it is preferred to maintain an interstitial space of at least 0.25 mm (0.010 in).

The braided material used to form the sheath advantageously has one or more of the following properties:

A braided tube that can expand to approximately 4 times its initial low profile diameter. This means when braided, it is made in its lowest profile diameter but with the application of compression (by pushing the ends towards each other), the diameter of the braided tube can expand to 4 times the diameter.

The braided tube has an outside diameter of approximately 10 mm (⅜ in.) and can expand to approximately 40 mm (1½ in.).

The braided tube has as a full load braid pattern, meaning that any individual strand passes over two strands and then under two strands and then back over two strands, with this path continuous throughout the braided tube and for each individual fiber.

The braided tube is made from 0.25 mm (0.010 in.) diameter, round PET (polyethylene terephthalate) monofilament.

The braided tube is made from 96 individual fibers.

The braided tube, when placed over a 25 mm diameter (1 in.) rod has approximately one pic per millimeter or 24-26 pics per one inch, i.e., the count of crossing pairs of fibers along a straight longitudinal line on the braid surface per unit length. It is a measure of the braid density at that particular diameter.

An access sheath that has a high coefficient of friction may impede free movement of surgical instruments. The sheath should also advantageously maintain lubricity for the entire duration of the surgical procedure, which may be several hours, with surgical instruments extended and withdrawn through the sheath multiple times. Lubricity refers to the friction occurring when an object (such as surgical tool) slide across the material of the sheath, i.e., how slippery the material is.

An access sheath without inherent lubricity requires use of an external surgical lubricant, or using water or saline solution as a lubricant. However, this requires repeated or continual application of the surgical lubricant or flushing of water or saline, to maintain consistent lubricity. Hence, using an external lubricant introduces an additional step to the surgical procedure, which slows the surgical procedure, while also potentially obscuring visualization of the surgical field.

A hydrophilic coating may optionally be applied to the surface of the access sheath. However, this requires wetting the device to activate the coating. Hydrophilic coatings may also decrease in lubricity over the course of a long procedure with large numbers of instrument passes.

The present sheath may be provided as a composite structure of a braided material and water proofing material. The water proofing material may be silicone. The present composite structure sheath can provide long lasting lubricity, in contrast a simple molded rubber access sheath. The present braided material composite sheath does not require the application of lubricants and maintains its performance throughout the length of the procedure.

The silicone (or equivalent material) may be applied to the braided material by dip coating. The silicone is provided to make the braided material water proof, i.e., in the sense of preventing water from passing through the braided material. The silicone is not needed to provide lubricity because the braided material itself provides lubricity. The silicone fills in the interstitial spaces between the fibers of the braided material. Advantageously, the silicone has a maximum layer thickness of 0.13 mm (0.0005 inches). Maximum layer thickness refers to the thickness of the silicone, not including the thickness of the braided material. Stated differently, advantageously the thickness of the silicone does not project above or below the fibers by more than 0.13 mm.

For example, if the braided material is made of fibers having a 0.25 mm (0.01 inch) diameter, the total thickness of the silicone is advantageously 0.25 mm to 0.51 mm. Excessive thickness of silicone (or equivalent material) decreases lubricity.

The composite sheath achieves its performance because it has a non-continuous contact surface. Rather, the surface is a series of distinct contact points due to the undulating surface texture created by the spaced apart fibers.

Instead of instruments contacting a flat surface of an elastomer, instruments have minimal contact area with the bumps formed by the crossing of round monofilament fibers. The sheath allows a high durometer and less tacky material (such as PET monofilaments) to still have the foldability, stretchability, and conformability, that would otherwise require an elastomer with a lubricant as described above.

Figure 24:
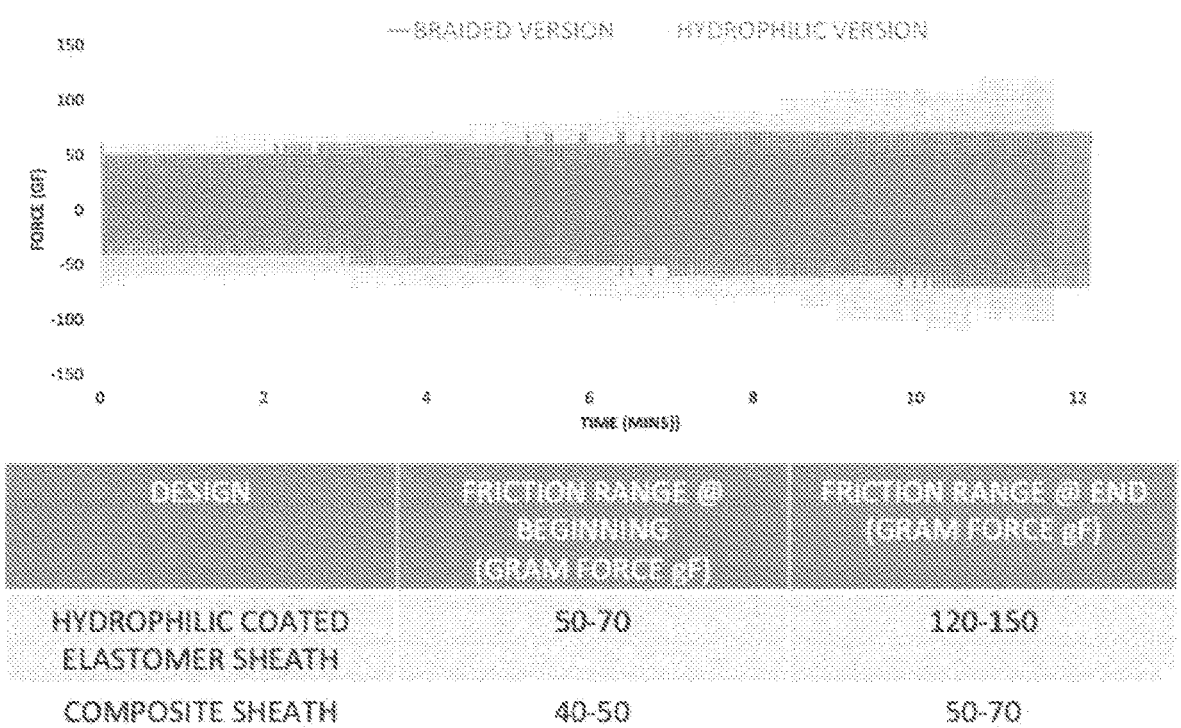
FIG. 24. is a graph of performance data of the sheath shown in FIG. 23.

FIG. 24 shows functional test data of a hydrophilic coated elastomeric sheath compared to the present inherently lubricious composite sheath. The test data was generated using a stainless steel rod representing an instrument applied with a normal load of 4.4 Newtons (1 pound force) while the instrument was passed forward and backward. FIG. 24 represents roughly 200 instrument passes representing a multi-hour procedure.

Figure 25:
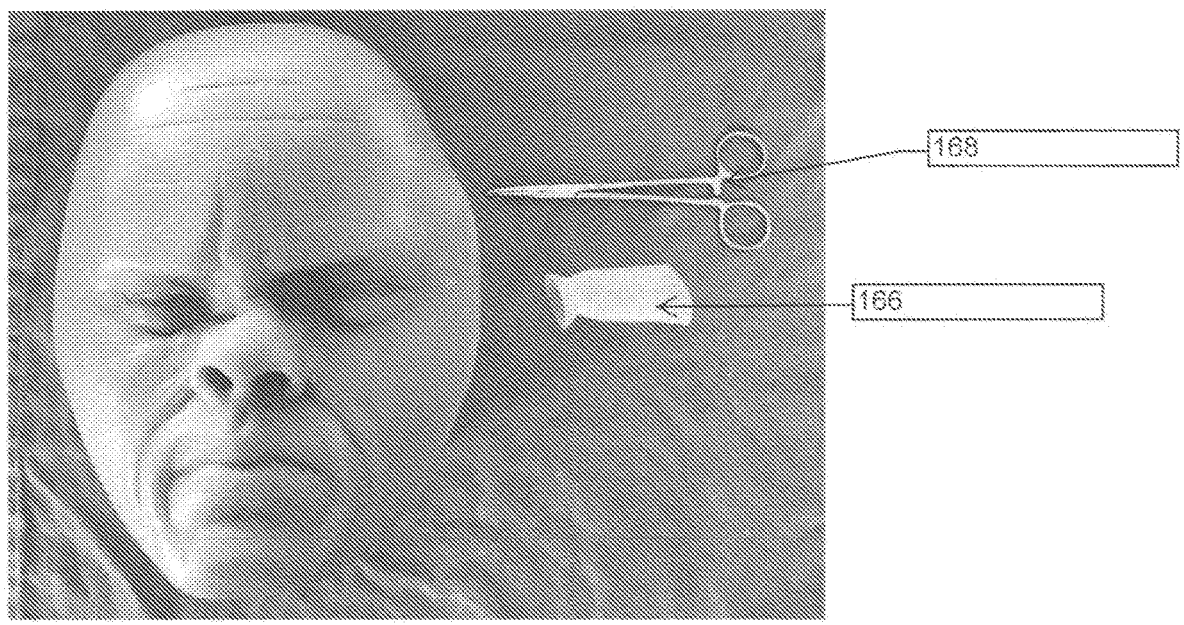
FIG. 25 is a plan view of the sheath shown in FIG. 23, with a surgical tool and a human nasal anatomy model.

A method of insertion, placement and deployment of a braided access sheath 166 is described below. This method uses a pulling force rather than a pushing force as the unique braided structure of the sheath will tend to resist pushing forces as the diameter of the sheath increases with pushing forces. FIG. 25 shows a nasal anatomy model with a braided access sheath 166 and a deployment tool. The braided access sheath 166 is shaped to generally match to the natural passageway of the sinus cavity. The top or superior side 172 has a hump 176 that follows the natural opening of the sinus cavity and allows the sheath to open and to provide greater working space. Referring momentarily back to FIG. 17 for example, the hump 176 is formed via the intersection of surfaces 152 and 154. Similar to the sheath of FIG. 17, the sheath 166 is also be vertically non-symmetrical about its centerline AN, i.e., the shape, orientation, and or dimensions of the top surface of the sheath are not the same as, and not mirror images of, the bottom surface of the sheath. Thus, for improved deployment, the sheath 166 is advantageously aligned (relative to sinus cavity) in a superior/inferior direction and then folded as shown in FIG. 26.

Figure 26:
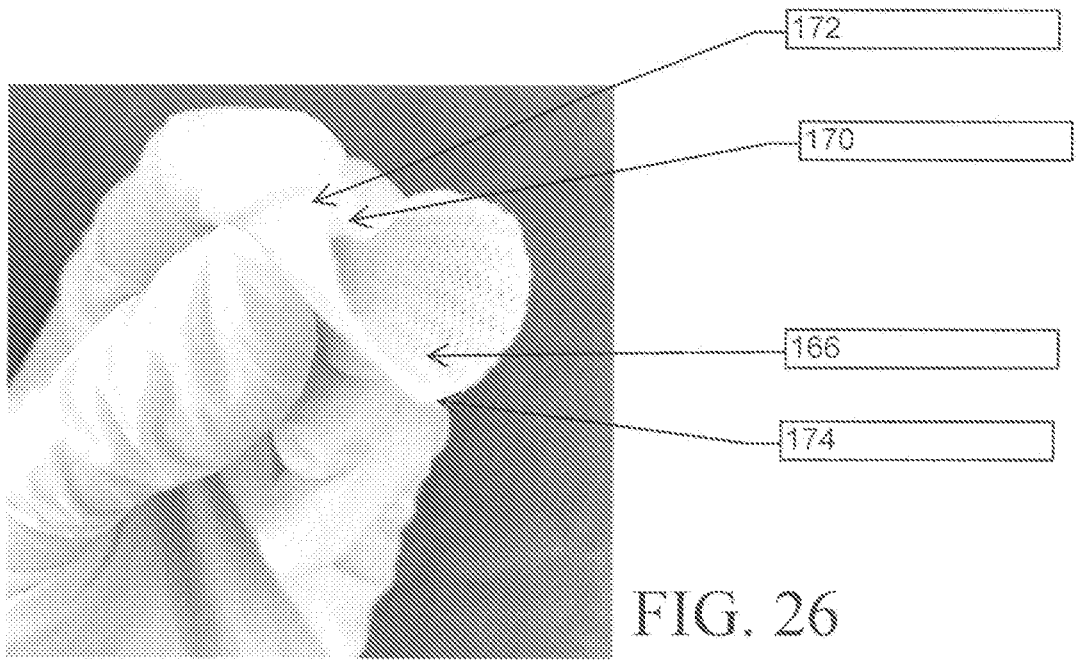
FIG. 26. is a perspective view of the sheath shown in FIGS. 23 and 25, with the sheath now folded by a gloved human hand.

FIG. 26 shows the braided access sheath 166 with the top of the sheath (superior side) being folded to the bottom (inferior side) to prepare for deployment. By folding the superior side 172 of the sheath to the inferior side 174 or vice versa, the sheath diameter is now capable of being inserted the naris of a patient.

Figure 27:
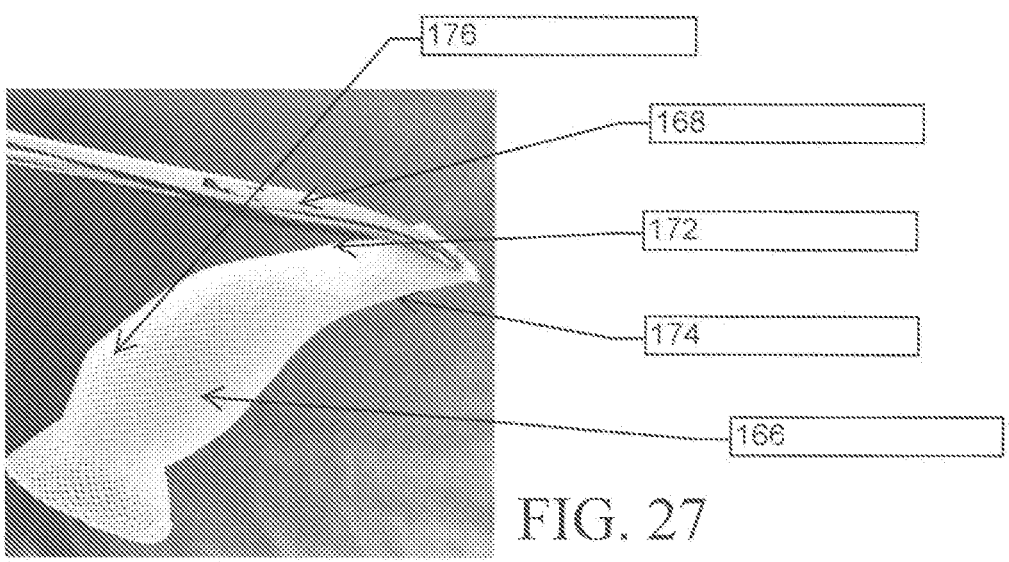
FIG. 27 is a perspective view of the folded sheath of FIG. 26 with the surgical tool of FIG. 25 grasping the folded end of the sheath.
Figure 28:
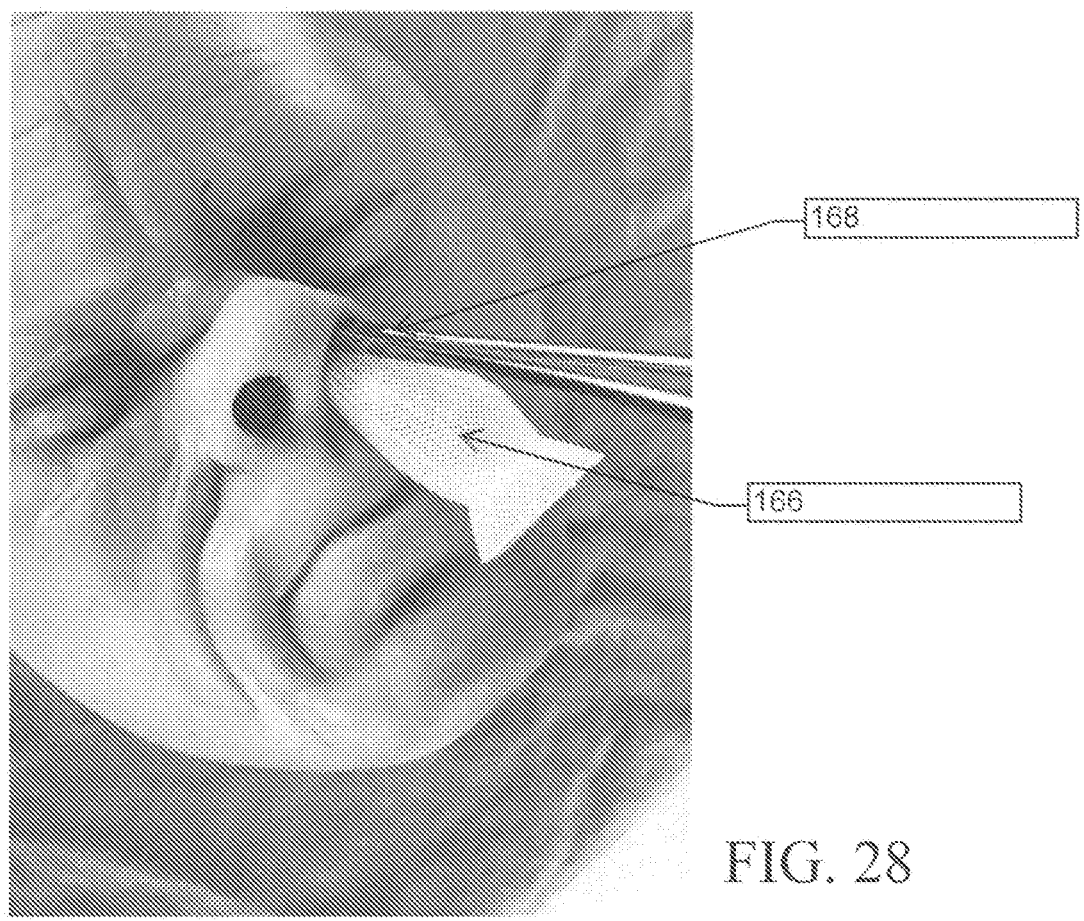
FIG. 28 is a perspective view of placement of the sheath of FIG. 27 using the surgical tool.
Figure 29:
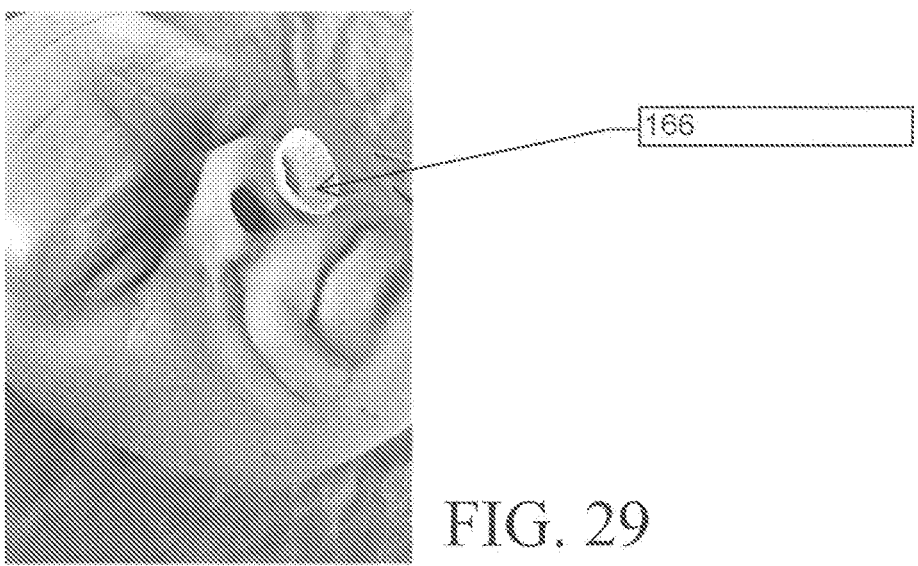
FIG. 29 is a perspective view of the sheath in place.

Once folded, the sheath 166 can be grasped and held in position with any standard medical tool 168 such as a pituitary forceps, a curved hemostat, a standard hemostat, or any medical instrument that can hold the folded sheath as shown in FIG. 27. Typically, the tool is used to grasp the folded distal end 170 of the access sheath 166. Using the tool 168, the sheath is then pulled into the sinus cavity either under the direct visualization of a scope or without as shown in FIG. 28. The sheath can be placed to user's preferred distal position. The sheath 166 may be adjusted distally or proximally until it is in the proper operating position as shown in FIG. 29. In FIG. 29, the sheath is deployed and expanded, with the sheath conforming to the nasal cavity and naris.

An access sheath may protect the anatomy from multiple passes of instruments, provide a hood to keep the scope clean, and minimize the run-in of blood to the operating site.

The run-in of blood into the operating site comes primarily from the anatomical dissection performed in the proximal sinus cavity prior to the placement of the access sheath. This may include the creation of a nasal flap, removal of turbinates or bleeding from instrument passage. Hence, the ability of an access sheath to stop or minimize blood run-in is advantageous.

Relative to blood run-in, an access sheath having a thin wall is provided, so that it can be folded into a minimum compact profile during placement but then have sufficient memory, expansion range, and expansion strength to expand against the anatomy when deployed. Expanding outwardly or splinting against the sinus cavity maximizes the open visual surgical field allowing better exposure for the surgery as well as providing a tamponading force against any bleeding in the proximal sinus cavity.

The access sheath may be made of a composite coated braid structure having a wall thickness of 0.38 mm to 0.88 mm (0.015 to 0.035 in.), or 0.52 to 0.72 mm (0.020 to 0.029 in.).

Correspondingly the access sheath has an expansion strength of 100-200 or 170 to 200 grams force as measured with a 3 mm (0.38 in.) rod pressing into the sheath at the longitudinal and vertical center of the sheath for 6 mm (0.25 in.) displacement. Expansion strength refers to the amount of outward force the sheath can exert on surrounding tissue. For sheaths having a generally oval cross section, for example as shown in FIG. 13B, 17, 21 or 29, expansion strength in the vertical direction (across the longer axis of the passageway through the sheath, in the direction of line F4 in FIG. 17), will be greater than the expansion strength in the lateral direction (laterally inwardly across the shorter axis of the passageway, in the direction of dimension WW in FIG. 19). Expansion strength as used here refers to minimum expansion strength, which will typically be the expansion strength in the lateral direction.

A metric on the splinting efficiency of the access sheath is expansion strength per unit of wall thickness, expressed as:

expansion strength/wall thickness=$T$ ratio in gm/mm.

For example, a sheath having an expansion strength of 190 gm and a 0.62 mm (0.025 in.) wall thickness would have a T ratio of 190 gm/0.62 mm=306 gm/mm]. Generally sheaths having a T ratio of about 200 to 400 may be used.

The sheath shown in FIGS. 23-29 is generally made of a combination of a single layered braid and an elastomeric coating which fills the interstitial spaces between the braided elements. This structure creates an embodiment with sufficient expansion strength to tamponade, splint open, and interlock with the anatomy. Either component of the composite structure can be adjusted to adjust the expansion strength. The monofilament size of the braid can be increased or decreased to increase or decrease the expansion strength. Similarly the thickness or durometer of the coating can be adjusted to increase or decrease the expansion strength. The preferred embodiment uses PET monofilaments of a diameter of 0.25 mm (0.010[ in.) and a coating thickness of less than 0.13 mm (0.005 in.) to produce specifications in a composite structure with wall thickness minimized and sufficient expansion strength.

An alternative embodiment is made of a single layer of braid material, such that the wall thickness of the sheath is equal to the diameter of the braid fibers plus the thickness of the layer or coating (e.g., silicone) on the inside and on the outside of the braid fibers. However, sheaths may optionally be made with two or more layers of braid material, over entire or substantially the entire sheath, or over selected portions of the sheath. For example, a central area of the sheath may have a narrow reinforcement band with a second layer of braid material, to locally increase expansion strength. Similarly, a reinforcement band of a second layer of material may be provided at the distal and/or proximal end of the sheath.

Along with splinting the anatomy to provide improved surgical access, the expansion strength of the access sheath provides a tamponade against the sinus nasal cavity anatomy wall. This helps reduce seeping of blood flow that could result from minor abrasions during placement of the access sheath and/or existing bleeding injuries. Tamponade of blood flow then results in a cleaner surgical field as migrating blood flow along the surface and to the distal end of the access sheath is minimized. Post surgery the sheath may be left in place to continue to tamponading, and as an aid to healing and recovery while providing an open breathing passageway to better allow the patient to breath more freely.

Additionally, the expansion strength and associated anatomical fill, helps to maintain the access sheath in position. If the access sheath conforms to and slightly impinges on the anatomy, it then forms an interlocking shape with the anatomy which tends to resist migration of the sheath.

Thus, a novel surgical sheath and methods have been shown and described. Each of the features described in association with a specific embodiment may of course also be used in other embodiments described. Various changes and substitutions may of course be made without departing from the spirit and scope of the invention. The invention, therefore, should not be limited except by the following claims and their equivalents.

The invention claimed is:

1. A method of using a surgical access sheath, comprising:
   forming a fold in a portion of the sheath, the rest of the sheath remaining unfolded;
   grasping the fold with a surgical tool;
   using the surgical tool to pull the sheath into a nasal cavity of a patient, with a proximal end of the sheath remaining outside of the nose of the patient;
   unfolding the sheath to allow the sheath to conform to the nasal cavity; and removing the surgical tool;
   wherein the fold is at a distal end of the sheath and is formed from a top of the sheath.

2. The method of claim 1 wherein the sheath is vertically non-symmetrical, further including aligning a top surface of the sheath with the superior side of nasal cavity before pulling the sheath into the nasal cavity.

3. A method of using a surgical sheath, comprising:
   grasping a first end of the sheath with a first surgical tool, the sheath comprising a single layer braid material and an elastomeric coating filling interstitial spaces in the single layer braid material;
   creating a fold at a first end of the sheath by folding a top of the sheath to a bottom of the sheath;
   using the first surgical tool to pull the sheath into a nasal cavity of a patient, with a second end of the sheath remaining outside of the nasal cavity of the patient;
   allowing the sheath to conform to the nasal cavity;
   removing the first surgical tool from the nose of the patient;
   inserting a second surgical tool through the sheath;
   inserting a third surgical tool through the sheath; and
   using the second and third surgical tools to perform surgery in the head of the patient.

4. The method of claim 3 further including angulating the second surgical tool relative to the third surgical tool.

5. The method of claim 4 further wherein the angulating step stretches the second end of the sheath.

6. The method of claim 3 wherein the sheath is vertically non-symmetrical, further including aligning a top surface of the sheath with the nasal cavity before pulling the sheath into the nasal cavity.

7. The method of claim 3 wherein the sheath is adapted to be folded into a minimum compact profile during placement and to have sufficient expansion strength to expand against the nasal cavity after the sheath is in the nasal cavity.

8. The method of claim 3 wherein the sheath has an expansion strength of 100-200 grams force.

9. The method of claim 8 wherein the sheath has an expansion strength/wall thickness T ratio of 200 to 400.

10. The method of claim 3 wherein the sheath comprises a composite coated braid structure having a wall thickness of 0.38 mm to 0.88 mm.

11. The method of claim 3 wherein the single layer braid material comprises polyethylene terephthalate monofilaments of a diameter of 0.2 to 0.3 mm and a coating thickness of less than 0.13 mm.

12. The method of claim 3 further including forming a fold in the first end of the sheath, grasping the fold at the first end of the sheath with the first surgical tool, and performing the steps of claim 3 in sequence.

13. The method of claim 3 wherein the sheath has a hump on a top of the sheath that follows a natural opening of the nasal cavity, the hump formed by an intersection of first and second surfaces of the sheath, further including aligning the top of the sheath with the nasal cavity before pulling the sheath into the nasal cavity.

14. A method of using a surgical sheath, comprising:
   creating a fold in the sheath by folding a top of the sheath to a bottom of the sheath;
   the sheath comprising a single layer braid material of interwoven fibers and an elastomeric coating filling interstitial spaces in the single layer braid material, the sheath vertically non-symmetrical, the sheath having an interior surface having an undulating surface texture created by the interwoven fibers;
   aligning a top surface of the sheath with the superior side of the nasal cavity of a patient;
   grasping the fold with a first surgical tool;
   using the first surgical tool to pull a first end of the sheath into the nasal cavity of the patient, with a second end of the sheath remaining outside of the nasal cavity of the patient;
   allowing the sheath to conform to the nasal cavity;
   removing the first surgical tool from the nose of the patient;
   inserting a second surgical tool through the sheath;
   inserting a third surgical tool through the sheath; and
   using the second and third surgical tools to perform surgery in the head of the patient.

15. The method of claim 14 wherein the braid material is a braided tube having interstitial spaces of 0.25 to 1.5 mm, the sheath having a wall thickness of 0.38 mm to 0.88 mm, and the sheath made of interwoven fibers having a diameter of 0.2 to 0.3 mm.

16. The method of claim 15 wherein the interstitial spaces are 0.5 to 0.75 mm.

* * * * *